US006846933B1

(12) United States Patent
Hearn

(10) Patent No.: US 6,846,933 B1
(45) Date of Patent: Jan. 25, 2005

(54) ANTIMYCOBACTERIAL COMPOUNDS AND METHOD FOR MAKING THE SAME

(75) Inventor: Michael J. Hearn, Needham, MA (US)

(73) Assignee: The Board of Trustees of Wellesley College, Wellesley, MA (US)

( * ) Notice: Subject to any disclaimer, the term of this patent is extended or adjusted under 35 U.S.C. 154(b) by 174 days.

(21) Appl. No.: 09/699,732

(22) Filed: Oct. 30, 2000

(51) Int. Cl.$^7$ .............................................. C07D 213/88
(52) U.S. Cl. ........................................................ 546/325
(58) Field of Search ........................................... 546/325

(56) References Cited

FOREIGN PATENT DOCUMENTS

JP 51032363 * 3/1976

OTHER PUBLICATIONS

CASREACT 134:24806, "Synthesis, characterization, and antitumour activity of isonicotinamido–4–bis (2–chloroethyl)aminobenzaldimine complexes of some transition metals", Li et. al., Chemical Papers (2000), 54 (4), 239–244.*

Journal of Organic Chemistry, vol. 18, Synthetic Tuberculostats. V. Alkylidene Derivatives of Isonicotinylhydrazine, p. 983–989 (1953).*

CA 12508g, "Aldehyde hydrazone derivatives in cancer chemotherapy", Wiley et. al., Vold. 58, 1963.*

Ca 14721c, "Aminooxides of physiologically active copounds. I. Aminooxides of isonicotinic acid derivatives.", vol. 51, 1957.*

Jahresbericht 1954/55 Chemi des Isoniazids, Ekkehard Kruger–Thiemer, Entdeckungsgeschichte, pp. 192–197 (English Translation Enclosed); pp. 229–232 (English Translation Enclosed); pp. 303–319.*

CA 2103f, "Material for electrophoographic reproduction", Schlesinger, vol. 56, 1962.*

CA 13326a, "Gossypol and isonicotinoylhydrazogossypol as analytical reagents for the photocolorimetric determination of uranium", Asamov et. al., vol. 59, 1964.*

CA 11458 f, "4–hydroxycoumarin derivatives wth anticoagulent activity. V. Condesation Products of aromatic dialdehydes with 4–hydroxycoumarin.", Pazdro et. al., vol. 59, 1963.*

Preparation and Spectroscopic Properties of 3–Acyl–1,3,4,–oxadiazolines, Department of Chemistry, Wellesley College, pp. 1647–1649, Sep.–Oct. 1995.

A convenient method for the preparation of tuberculostatic diacylhydrazines, Bull. Soc. Chim. Belg., vol. 106 No. 2, 1997, pp. 109–114.

Jahresbericht Borstel, 1956/57, Biochemie des Isoniazids, pp. 331–338 (English Translation Enclosed); pp 410–414 (English Translation Enclosed).

Isonicotinoyl hydrazones and their antituberculous activity, Doklady Akad. Nauk S.S.s.R. 84, 981–4 (1952) (Abstract Only).

Antibacterial action of amphipathic derivates of isoniazid against the Mycobacterium avium complex, Zntralbl. Bakteriol, Mikrobiol. Hyg., Ser. A (1988), 268(4), 456–62 (Abstract Only).

(List continued on next page.)

*Primary Examiner*—Joseph K. McKane
*Assistant Examiner*—Binta Robinson
(74) *Attorney, Agent, or Firm*—Gauthier & Connors LLP

(57) ABSTRACT

The present invention relates to novel antimycobacterial compounds and in particular to antimycobacterial compounds comprised of Schiff base, diacylhydrazine, sulfur-containing diacylhydrazine and oxadiazoline congeners of isonicotinic acid hydrazide. This invention further relates to processes for their preparation, to intermediates useful in their preparation, to their use as therapeutic agents and to pharmaceutical compositions containing them.

7 Claims, 2 Drawing Sheets

OTHER PUBLICATIONS

Synthetic Tuberculostats. V. Alkylidene Derivatives of Isonicotinylhydrazine, Journal of Organic Chemistry, vol. 18, pp. 983–989 (1953).

Buu–Hoi et al., Tuberculostatic Hydrazides and their Derivatives, Journal of the Chemical Society, (278) 1358–1364 (1952).

Chemotherapy of Experimental Tuberculosis. VIII. The Synthesis of Acid Hydrazides, their Derivatives and Related Compounds, Journal of the American Chemical Society, pp. 1933–1942 (1953).

Stability and Antibacterial Effect of D–Glucuronolactone Isonicotinyl Hydrazone and Isoniazid, American Review of Tuberculosis of Puluronary Disease, vol. 73, 1956 (pp. 892–906).

Effects of Isoniazid on Ultrastructure of Mycobacterium aurum and Mycobacterium tuberculosis and on Production of Secreted Proteins, Antimicrobial Agents and Chemotherapy, Nov. 1996, pp. 2459–2467.

Mycolic Acids: structure, biosynthesis and physiological functions, Prog. Lipid Res., vol. 37, No. 2/3, pp. 143–179 (1998).

Crystal Structure of the Mycobacterium tuberculosis Enoyl–ACP Reductase, InhA, in Complex with NAD and a C16 Fatty Acyl Substrate, The Journal of Biological Chemistry, vol. 274, No. 22, May 28, pp. 15582–15589 (1999).

Using near infrared spectroscopy to monitor the preparation of compounds for screening as antituberculosis drugs, Journal of Near Infrared Spectroscopy, 3, 19–23 (1995).

Fox, H.H. et al.: Synthetic tuberculostats. V. Alkylidene derivatives of isonicotinylhydrazine. J. Org. Chem. vol. 18, pp. 983–989, 1953, especially compounds in tables I, II and III on pp. 985 and 986.

Bottari, B. et al. Isoniazid–related copper (II) and nickel (II) complexes with antimycobacterial in vitro activity. Bioorgan. & Medicin. Chem. Lett. 2000, vol. 10, pp. 657–660, especially compounds 1a–1n in scheme 1 on p. 658.

Experimentelle vergleichende Untersuchung der tuberkulostatischen Wirksamkeit nd Toxizitat von INH, INHG and INHG–Na, pp. 409–416, Arzneim. Forsch., vol. 26, No. 3 (1976) (Abstract Only).

Reactions of the hydrazine derivatives, Univ., Ser. Mat., Mekh., Astron., Fiz I Khim. 14, No. 4, 187–93 (19, Univ., Ser. Mat., Mekh., Astron., Fiz I Khim. 14, No. 4, 187–93 (1959) (Abstract Only).

* cited by examiner

* 1 dead at each 11, 17, 18 and 22 days post-infection

** 1 dead at 9 days post-infection

*** 1 dead at 11 days post-infection

ANTIMYCOBACTERIAL COMPOUNDS AND METHOD FOR MAKING THE SAME

BACKGROUND OF THE INVENTION

1. Field of the Invention

The present invention relates to novel antimycobacterial compounds and in particular to antimycobacterial compounds comprised of Schiff base, diacylhydrazine, sulfur-containing diacylhydrazine and oxadiazoline congeners of isonicotinic acid hydrazide. This invention further relates to processes for their preparation, to intermediates useful in their preparation, to their use as therapeutic agents and to pharmaceutical compositions containing them.

2. Description of the Related Art

The occurrence of some three million new cases of tuberculosis per year world-wide and the emergence of new strains of *Mycobacterium tuberculosis* characterized by drug resistance or increased virulence have created the need for the evolution of newer and more powerful drugs, the re-examination and re-evaluation of prior art drugs and the detailed elucidation of the mechanisms of action of antimycobacterial compounds.

In the United States there has been an increase in the incidence of tuberculosis between 1985 and 1992. As many as 15 million persons in the United States are probably infected but are not yet symptomatic. These persons may develop active disease, and their risk for so doing increases when coinfected with the human immunodeficiency virus (HIV). Infection with *Mycobacterium tuberculosis* is observed to a significant extent among acquired immune deficiency syndrome (AIDS) patients or among individuals undergoing immunosuppressive therapy. Significantly, tuberculosis accelerates the natural history of HIV, particularly in the early stages of infection, resulting in an increased viral load. Tuberculosis may generate a nurturing microenvironment for HIV, enhancing viral replication. While many cases of disease due to pathogenic mycobacteria are caused by *Mycobacterium tuberculosis* (MTB), several other mycobacterial diseases have begun to emerge, caused by nontuberculous mycobacteria (NTB). These include diseases caused by *Mycobacterium avium, M. ulcerans, M. marinum* and *M. haemophilum*. These NTM diseases are considered important opportunistic infections (OIs) in patients with AIDS, but the rates of non-AIDS-associated NTB infections are also on the rise.

An absence of activity by those skilled in the art in the area of new drug development extending over a period of approximately 35 years has led to minimal research relating to the design of new antimycobacterial agents. This lack of research is a result of the usefulness and efficacy of prior art drugs such as isoniazid (INH, the most widely used antimycobacterial drug), ethambutol, rifampin and pyrazinamide. Combination therapy involving these drugs, especially when prescribed as one component of a broader therapeutic regimen such as directly-observed short-course therapy (DOTS), has been highly effective. When the goal of the elimination of tuberculosis seemed achievable, based largely on these effective drugs and improving standards of nutrition, hygiene and public health, little impetus remained for research.

Today, it is clear that increased research on drug design has been necessary to recapture lost ground and to make new advances. To facilitate the development of new antimycobacterials, those skilled in the art have recently begun to place strong emphasis on the identification of the targets of existing drugs and on those characteristics of pathogen cell wall structure that play a role in limiting drug effectiveness. Billington et al., Synthesis and Antimycobacterial Activity of Some Heteroarylcarboxamidrazone Derivatives. Drug Design and Discovery. 15:269–275 (1998); Setlow P., Survival of Dormant Spores of *Bacillus* Species for Years and Years and . . . How Do They Do It? The Nucleus. LXIII:5 (1995); Wallis et al., Drug Tolerance in *Mycobacterium tuberculosis*. Antimicrobial Agents and Chemotherapy. 43(11):2600–2606 (1999). For example, one target enzyme for INH is a long-chain enoyl-acyl carrier protein (ACP) reductase (InhA). This enzyme is important for the biosynthesis of mycolic acids, alpha-branched fatty acids containing as many as 90 carbon atoms, crucial components of mycobacterial cell walls. Asselineau, J. et al., Chemical Structure and Biological Activity of Mycolic Acids, p. 14ff, 40. In C. Wolstenholme, M. Cameron, and C. O'Connor (ed.), Ciba Foundation Symposium on Experimental Tuberculosis: *Bacillus* and Host (with an Addendum on Leprosy)(1955); Brennan, P. et al., The Envelope of *Mycobacteria*. Annual Reviews in Biochemistry. 64:29–63 (1995).

The present invention provides novel Schiff base, diacylhydrazine, sulfur-containing diacylhydrazine and oxadiazoline congeners of isonicotinic acid hydrazide that have increased lipophilicity and inhibit mycolate biosynthesis.

In addition to the need for the evolution of newer and more powerful antimycobacterial drugs, the biological evaluation of compounds suspected to be active against mycobacteria requires that the compounds be readily available in pure form on quantity scale, generally understood to be gram or multi-gram scale, as opposed to milligram scale. Gram scale quantities are necessary for the large numbers of biological tests which must be performed and replicated for the evaluation of a new drug candidate.

Products of synthetic reactions are most desirable when they can be easily and cheaply obtained as dry and free-flowing solids. In the long run, dry and free-flowing solids permit better formulations of drugs as tablets, capsules or syrups. The invention disclosed herein provides a novel method of Schiff base synthesis which yields products directly as dry free-flowing solids in analytically pure form. The products of the prior art syntheses are obtained as intractable oils which are difficult and labor-intensive to purify or bring into dry free-flowing form. The present invention overcomes these drawbacks and provides syntheses of Schiff base, diacylhydrazine, sulfur-containing diacylhydrazine and oxadiazoline congeners of isonicotinic acid hydrazide, which yield products that are suitable for biological evaluation.

BRIEF SUMMARY OF THE INVENTION

Broadly, this invention comprises compositions having efficacy against mycobacterial infections. One aspect of the invention comprises the rational design of more potent and less toxic antimycobacterial drugs using synthetic organic chemistry. Such drugs can achieve improved outcome against mycobacteria by increasing drug lipophilicity. Rational design choices allow the inclusion into drug structure of elements promoting diffusion across the mycobacterial cell wall through the lipid domain. The resulting enhanced activity will permit lower dosing and greater tolerance by the host. In addition to the lipophilic units, the structures of many of these compounds also incorporated multiple-bonding sites which render them potential substrates for reductases and thus possible oxidative stressors of mycobacteria.

Another aspect of the invention comprises the reliable and reproducible methods for the synthesis of these compounds on such a scale and in such purity as to be suitable for subsequent biological evaluations, such as evaluations using near infrared spectroscopy (NIR), so compounds can be readily obtained on multigram scale and in good purity. The syntheses of the invention obviate the need for special drying, mulling or pelleting of samples for spectrometric techniques, such as mid-range infrared spectroscopy. Also within the scope of the invention is a method for quantitative estimates of the relative lipophilicities of the antimycobacterial compounds which comprises partitioning the antimycobacterial compounds between organic and aqueous phases in biphasic liquid-liquid extraction. Antimycobacterial compounds can be isolated from each of the phases, and the ratio of amounts in each phase can be compared to a similar ratio for INH as standard.

Another aspect of this invention comprises the syntheses for the preparation of Schiff base, diacylhydrazine, sulfur-containing diacylhydrazine and oxadiazoline congeners of isonicotinic acid hydrazide.

Yet another aspect of this invention comprises the intermediates useful in the syntheses of Schiff base, diacylhydrazine, sulfur-containing diacylhydrazine and oxadiazoline congeners of isonicotinic acid hydrazide.

The present invention provides useful antimycobacterial compounds which are effective against a number of species of mycobacteria.

Another aspect of the invention provides useful antimycobacterial compounds which are unexpectedly effective against *Mycobacterium tuberculosis, Mycobacterium kansasii*, and *Mycobacterium avium.*

This invention also comprises pharmaceutical compositions containing Schiff base, sulfur-containing diacylhydrazine and oxadiazoline congeners of isonicotinic acid hydrazide and their use as therapeutic agents for the treatment of mycobacterial infections.

Another aspect of the invention comprises the formula:

I

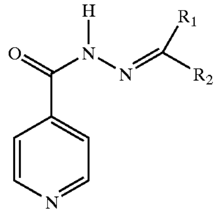

wherein $R_1$ is H; and $R_2$ is $C_3$ to $C_{14}$ alkyl, $C_3$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle, halo, hydroxy, amino, or carboxy;

or a pharmaceutically acceptable salt thereof; or a pharmaceutical isomer thereof; or a combination of the same.

Another embodiment of the invention comprises formula I wherein $R_1$=H, and $R_2$ is CH═$CHCH_3$ (trans), CH═$CHCH_2CH_3$ (trans), CH═$CHCH_2CH_2CH_3$ (trans), CH═$CHCH_2CH_2CH_2CH_3$ (trans), $C(CH_3)$═$CHCH_3$ (trans), CH═$C(CH_3)CH_2CH_2CH$═$C(CH_3)_2$ (trans), CH═NNHCO-4-$C_5HN$, $CH_2CH(CH_3)CH_2CH_2CH$═C$(CH_3)_2$, 4-$C_6H_4$—CH═NNHCO-4-$C_5H_4N$, 4-$C_6H_4$—O—$CH_2CH_2CH_2CH_3$, $(CH_2)_{11}CH_3$, 4-$C_6H_4NO_2$, $C_6H_5$, 2-$C_6H_{40}H$, 4-OH-3-$OCH_3C_6H_3$, 4-$C_6H_4OCH_3$, 3-$C_6H_4OCH_3$, $(CH_2)_{11}CH_3$, $(CH_2)_2CH_3$, 2-$C_6H_{40}CH_3$, $C(CH_3)$═$CHC_6H_5$ (trans), 4-$C_6H_4F$, 3,5-di$(CH_3)$-4-O—$C_7H_7$, 2-F-4-$OCH_3C_6H_3$, 2-$ClC_6H_{4,4}$-$BrC_6H_{4,3}$-$C_6H_4NO_2$, 4-$C_6H_4O(CH_2)_5CH_3$, 2-$C_{1-5}$-$NO_2C_6H_3$, 4-$C_{1-3}$-$NO_2C_6H_3$, 2-$C_6H_4NO_2$, 2-6-di(Cl)$C_6H_3$, 2,3-di(Cl)$C_6H_3$, $C_6H_5$, 3,4-di(F)$C_6H_3$, 2,6-di(F)$C_6H_3$, 3,4-di(Cl)$C_6H_3$, 4-$C_6HCl$, or CH═$C(C_6H_5)_2$.

Yet another embodiment of the invention comprises formula I wherein $R_1$ is $CH_3$ and $R_2$═$CH_2COCH_3$ or $C_6H_5$.

In yet another embodiment, the invention comprises formula I wherein $R_1$ is $CH_2CO_2CH_2CH_3$ and $R_2$ is $CH_2CH_2CH_3$ or $CH_3$.

Yet another embodiment of the invention comprises formula I wherein $R_1$ is $CO_2CH_2CH_3$ and $R_2$ is $CH_2CH_2C_6H_5$.

Another embodiment of the invention comprises formula I wherein $R_1$ is 2-$C_5H_4N$ and $R_2$ is 2-$C_5H_4N.2H_2O$.

Yet another embodiment of the invention comprises formula I where $R_1$,$R_2$ is $(CH_2)_4$, $(CH_2)_6$, 4-$C_6H_8NNHCO$-4-$C_5H_4N$.

Another embodiment of the invention comprises formula I where $R_1$,$R_2$ is

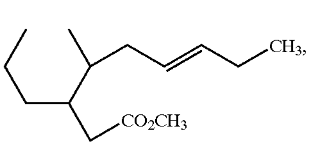

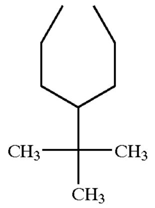

or

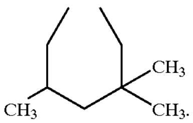

Another embodiment of the invention comprises formula I wherein $R_1$ is H; and $R_2$ is

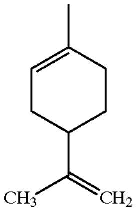

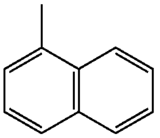

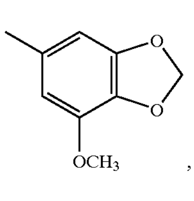

,

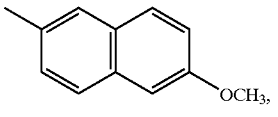

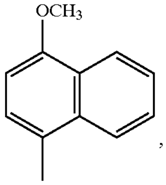

, or

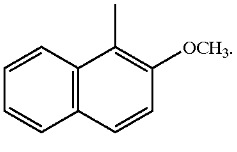

Another embodiment of the invention comprises the formula:

II

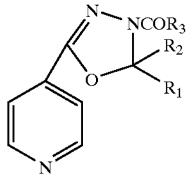

wherein $R_1$ is H; $R_2$ is $C_3$ to $C_{14}$ alkyl $C_3$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_6$ substituted phenylalkyl, benzyl, substituted benzyl, naphthyl, substituted naphthyl, heterocycle, substituted heterocycle; and $R_3$ is C, or $C_2$ alkyl; or a pharmaceutically acceptable salt thereof; or a pharmaceutically acceptable isomer thereof; or a combination of the same.

Yet another embodiment of the invention comprises formula II wherein $R_1$ is H, $R_2$ is 2,6-di(Cl)$C_6H_3$, 3-$NO_2$, 4-$C_1$—$C_6H_3$, 3,4-di(F)$C_6H_3$, 2-$C_6H_4NO_2$, 3,4-di(Cl)$C_6H_3$ and 2,6-di(F)$C_6H_3$ and $R_3$ is $CH_3$.

Yet another embodiment of the invention comprises formula II wherein $R_1$ is $CH_3$; $R_2$ is $CH_3$ and $R_3$ is $CH_2CH_3$ or $CH_3$.

Another embodiment of the invention comprises formula II wherein $R_1$, $R_2$ is $(CH_2)_5$ and $R_3$ is $CH_3$.

Yet another embodiment of the invention comprises formula II wherein $R_1$ is $CH_3$, $R_2$ is $C_6Hs$ and $R_3$ is $CH_3$.

Another embodiment of the invention comprises the formula:

III

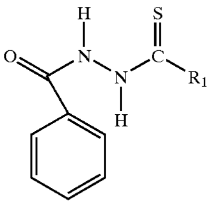

wherein $R_1$ is $C_2$ to $C_6$ alkyl, $C_2$ to $C_6$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle;

or a pharmaceutically acceptable salt thereof; or a pharmaceutically acceptable isomer thereof;

or a combination of the same.

Yet another embodiment of the invention comprises formula III wherein $R_1$ is $NHC_6H_5NH$-4—$C_6H_4CH_3$, NH-4—$C_6H_4Br$ or NH-4-$C_6HCl$.

The compounds of the present invention show enhanced and unexpected activity against several species of mycobacteria.

One embodiment the invention comprises a compound of the formula:

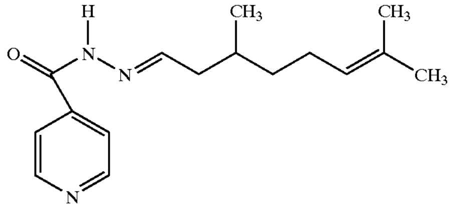

wherein the compound exhibits unexpected activity against mycobacteria selected from the group consisting of *M. avium* and *M. tuberculosis*.

Another embodiment of the invention comprises a compound of the formula:

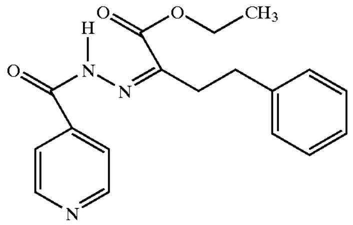

wherein the compound exhibits unexpected activity against mycobacteria selected from the group consisting of *M. avium* and *M. tuberculosis*.

Another embodiment of the invention comprises a compound of the formula:

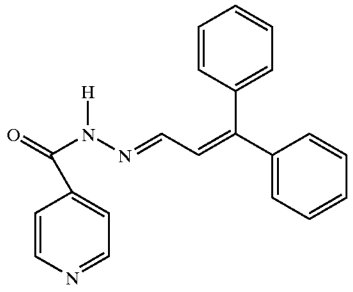

wherein the compound exhibits unexpected activity against mycobacteria selected from the group consisting of *M. avium* and *M. tuberculosis*.

Another embodiment of the invention comprises a compound of the formula:

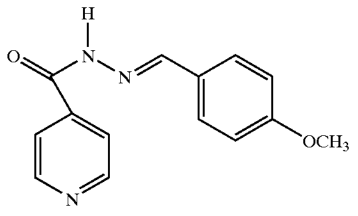

wherein the compound exhibits unexpected activity against mycobacteria selected from the group consisting of *M. avium* and *M. tuberculosis*.

Another embodiment of the invention comprises a compound of the formula:

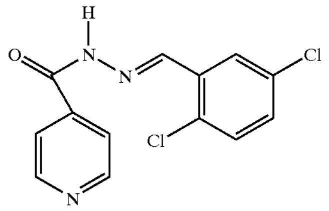

wherein the compound exhibits unexpected activity against mycobacteria selected from the group consisting of *M. avium* and *M. tuberculosis.*

Another embodiment of the invention comprises a compound of the formula:

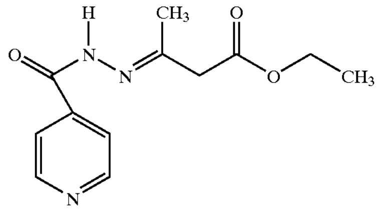

wherein the compound exhibits unexpected activity against mycobacteria selected from the group consisting of *M. tuberculosis.*

Another embodiment of the invention comprises a compound of the formula:

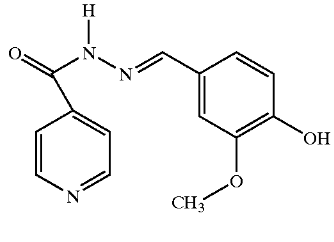

wherein the compound exhibits unexpected activity against mycobacteria selected from the group consisting of *M. tuberculosis.*

Another embodiment of the invention comprises a compound of the formula:

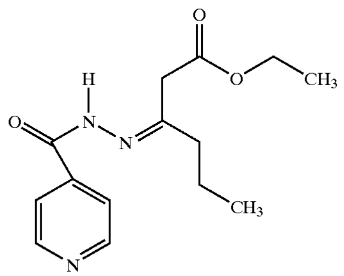

wherein the compound exhibits unexpected activity against mycobacteria selected from the group consisting of *M. tuberculosis.*

Another embodiment of the invention comprises a compound of the formula:

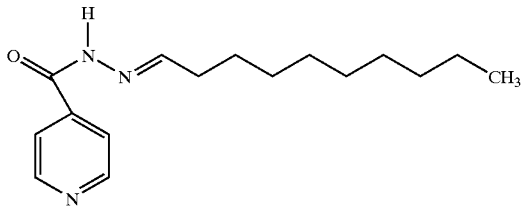

wherein the compound exhibits unexpected activity against mycobacteria selected from the group consisting of *M. tuberculosis.*

Another embodiment of the invention comprises a compound of the formula:

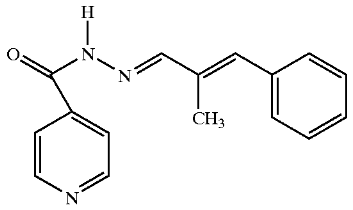

wherein the compound exhibits unexpected activity against mycobacteria selected from the group consisting of *M. tuberculosis.*

Another embodiment of the invention comprises a compound of the formula:

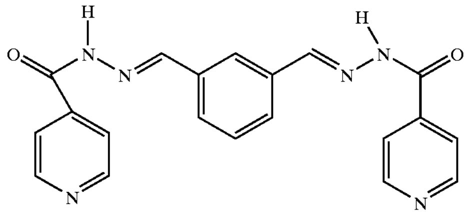

wherein the compound exhibits unexpected activity against mycobacteria selected from the group consisting of *M. tuberculosis.*

Another embodiment of the invention comprises a compound of the formula:

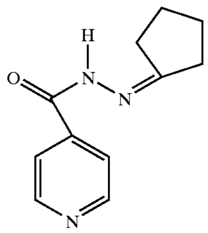

wherein the compound exhibits unexpected activity against mycobacteria selected from the group consisting of *M. tuberculosis.*

Another embodiment of the invention comprises a compound of the formula:

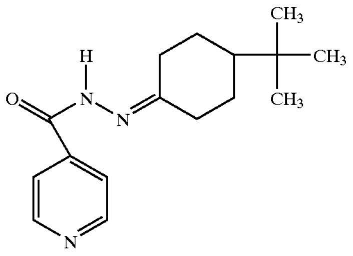

wherein the compound exhibits unexpected activity against mycobacteria selected from the group consisting of *M. tuberculosis.*

Another embodiment of the invention comprises a compound of the formula:

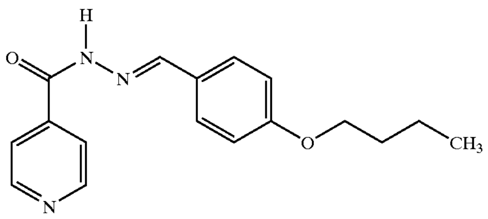

wherein the compound exhibits unexpected activity against mycobacteria selected from the group consisting of *M. tuberculosis.*

Another embodiment of the invention comprises a compound of the formula:

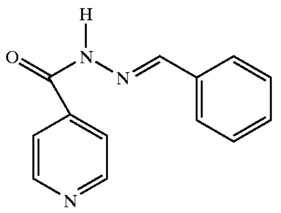

wherein the compound exhibits unexpected activity against mycobacteria selected from the group consisting of *M. tuberculosis.*

Another embodiment of the invention comprises a compound of the formula:

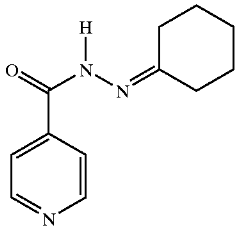

wherein the compound exhibits unexpected activity against *M. tuberculosis, M. avium* and *M. Kansasii.*

Another embodiment of the invention comprises a compound of the formula:

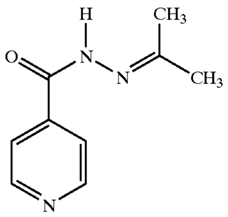

wherein the compound exhibits unexpected activity against *M. tuberculosis, M. avium* and *M. Kansasii.*

Another embodiment of the invention comprises a compound of the formula:

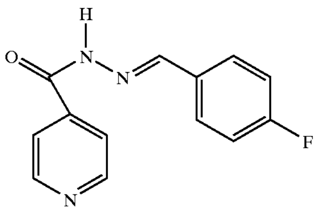

wherein the compound exhibits unexpected activity against mycobacteria selected from the group consisting of *M. tuberculosis.*

Another embodiment of the invention comprises a compound of the formula:

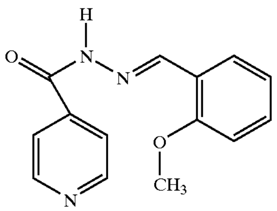

wherein the compound exhibits unexpected activity against mycobacteria selected from the group consisting of *M. tuberculosis.*

Another embodiment of the invention comprises a compound of the formula:

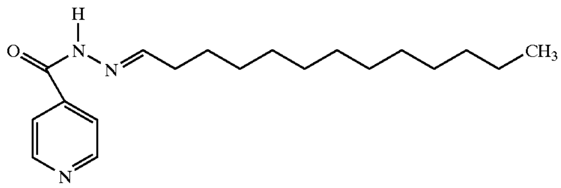

wherein the compound exhibits unexpected activity against mycobacteria selected from the group consisting of *M. tuberculosis.*

Another embodiment of the invention comprises a compound of the formula:

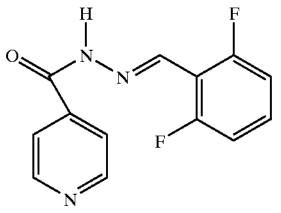

wherein the compound exhibits unexpected activity against mycobacteria selected from the group consisting of *M. tuberculosis* and *M. avium.*

Another embodiment of the invention comprises a compound of the formula:

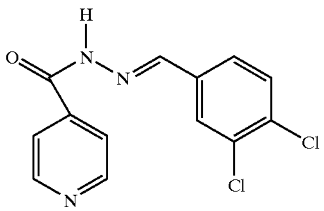

wherein the compound exhibits unexpected activity against mycobacteria selected from the group consisting of *M. tuberculosis* and *M. avium.*

Another embodiment of the invention comprises a compound of the formula:

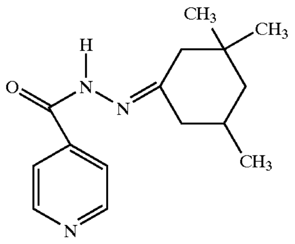

wherein the compound exhibits unexpected activity against mycobacteria selected from the group consisting of *M. tuberculosis, M. kansasii* and *M. avium.*

Another embodiment of the invention comprises a compound of the formula:

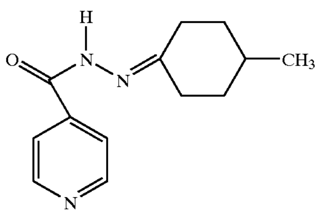

wherein the compound exhibits unexpected activity against mycobacteria selected from the group consisting of *M. kansasii.*

Yet another embodiment of the invention comprises a compound of the formula:

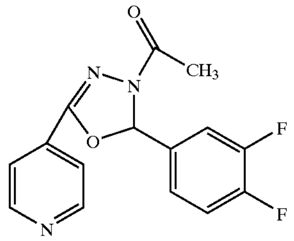

wherein the compound exhibits unexpected activity against mycobacteria selected from the group consisting of *M. tuberculosis* and *M. avium.*

Another embodiment of the invention comprises a compound of the formula:

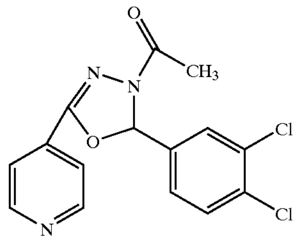

wherein the compound exhibits unexpected activity against mycobacteria selected from the group consisting of *M. tuberculosis* and *M. avium.*

Another embodiment of the invention comprises a compound of the formula:

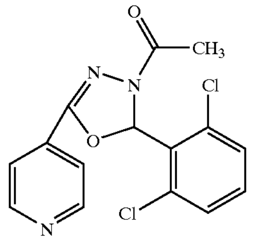

wherein the compound exhibits unexpected activity against mycobacteria selected from the group consisting of *M. avium.*

Another embodiment of the invention comprises a compound of the formula:

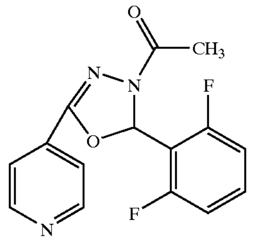

wherein the compound exhibits unexpected activity against mycobacteria selected from the group consisting of *M. tuberculosis.*

Another embodiment of the invention comprises a compound of the formula:

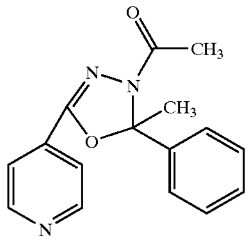

wherein the compound exhibits unexpected activity against mycobacteria selected from the group consisting of *M. tuberculosis*.

Another embodiment of the invention comprises a compound of the formula:

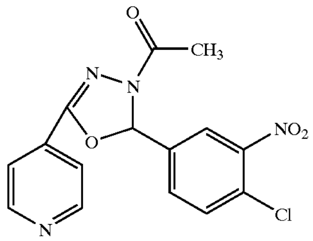

wherein the compound exhibits unexpected activity against mycobacteria selected from the group consisting of *M. tuberculosis*.

Another embodiment of the invention comprises a compound of the formula:

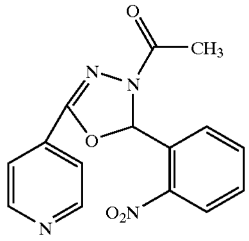

wherein the compound exhibits unexpected activity against mycobacteria selected from the group consisting of *M. tuberculosis*.

Yet another embodiment of the invention comprises a compound of the formula:

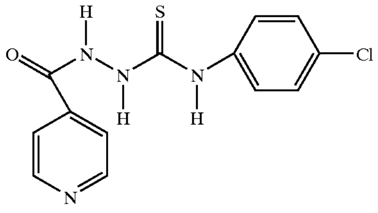

wherein the compound exhibits unexpected activity against mycobacteria selected from the group consisting of *M. tuberculosis*.

Another embodiment of the invention comprises a compound of the formula:

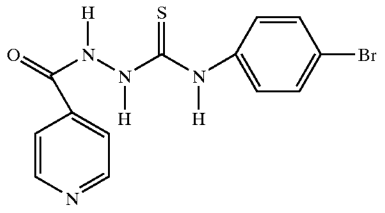

wherein the compound exhibits unexpected activity against mycobacteria selected from the group consisting of *M. tuberculosis*.

Another embodiment of the invention comprises a compound of the formula:

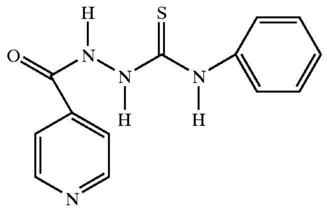

wherein the compound exhibits unexpected activity against mycobacteria selected from the group consisting of *M. tuberculosis*.

Suitable pharmaceutically-acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically-acceptable salt is the sodium salt.

It is to be understood that certain compounds of the formulas I, II and III can exist in solvated as well as unsolvated forms such as, for example, hydrated forms. It is also to be understood that the invention encompasses all such solvated forms which possess antimycobacterial activity.

It is also to be understood that the invention relates to all tautomeric forms of compound of formulas I, II, and III that posses antimycobacterial activity. More particularly, it is to be understood that the invention encompasses all optical, diastereo- and regio-isomers of formulas I, II, and III that possess antimycobacterial activity.

Another aspect of the invention relates to the syntheses of Schiff base, sulfur-containing diacylhydrazine and oxadiazoline congeners of isonicotinic acid hydrazide.

Yet another aspect of the invention comprises a method for the synthesis of antimycobacterial compounds comprising the formula:

I

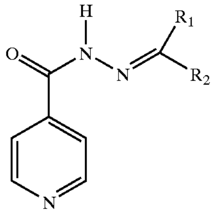

wherein $R_1$ is H or $CH_3$; and wherein $R_2$ is $C_1$ to $C_{14}$ alkyl, $C_2$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_6$ substituted phenylalkyl, benzyl, substituted benzyl, naphthyl, substituted naphthyl, heterocycle, substituted heterocycle, halo, hydroxy, amino, or carboxy; or wherein $R_1R_2$=$C_4$ to $C_8$ cycloalkyl or $C_4$ to $C_{10}$ substituted cycloalkyl;

which comprises refluxing (1)

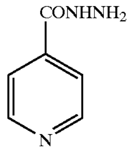

with absolute ethanol to produce a solution and adding a carbonyl compound comprising the formula of:

$$R_3COR_4 \qquad (2)$$

wherein $R_3$=H or $CH_3$; and wherein $R_4$=$C_1$ to $C_{14}$ alkyl, $C_2$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle, halo, hydroxy, amino, or carboxy; or wherein $R_3$ and $R_4$_=$C_4$ to $C_8$ cycloalkyl or $C_4$ to $C_{10}$ substituted cycloalkyl;

to the solution to produce a reaction mixture. The reaction mixture is distilled and diethyl ether is added to the reaction mixture. The reaction mixture is then filtered and the resulting filtrate is then dried to produce I.

Yet another embodiment of the invention comprises a method for producing an antimycobacterial compound comprising the formula of:

II

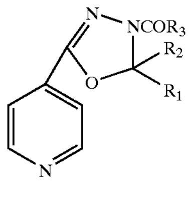

wherein $R_1$=wherein $R_1$ is H or $CH_3$ wherein $R_2$=$C_1$ to $C_{14}$ alkyl, $C_2$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle, halo, hydroxy, amino, or carboxy; or wherein $R_1R_2$=$C_4$ to $C_8$ cycloalkyl or $C_4$ to $C_{10}$ substituted cycloalkyl;

wherein $R_3$=$C_1$ or $C_2$ alkyl which comprises refluxing

I

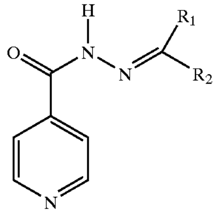

wherein $R_1$ is H or $CH_3$; and wherein $R_2$ is $C_1$ to $C_{14}$ alkyl, $C_2$ to $C_{10}$ substituted alkyl, $C_2$ to $C_{11}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_6$ phenylalkyl, $C_7$ to $C_{16}$ substituted phenylalkyl, benzyl, substituted benzyl, naphthyl, substituted naphthyl, heterocycle, substituted heterocycle, halo, hydroxy, amino, or carboxy; or wherein $R_1R_2$=$C_4$ to $C_8$ cycloalkyl or $C_4$ to $C_{10}$ substituted cycloalkyl;

with a carboxylic acid anhydride comprising the formula of:

$$(RCO)_2O \qquad (3)$$

wherein R=$C_1$ or $C_2$ alkyl to produce a reaction mixture. The reaction mixture is dried and ether is added to the dried reaction mixture to form a solution. The ether is separated from the solution to yield an aqueous layer. The aqueous layer is extracted with ether and the resulting ether extracts are dried to produce II.

Another embodiment of the invention comprises a method for producing an antimycobacterial compound comprising the formula of:

III

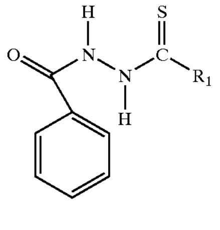

wherein $R_1$ $C_1$ to $C_6$ alky, $C_2$ to $C_6$ substituted alkyl, $C_2$ to $C_{10}$alkenyl, $C_2$ to $C_{10}$ substituted alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle;

which comprises refluxing

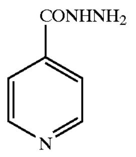
(I)

with ethanol to produce a solution and adding an isothiocyanate comprised of the formula of:

$$RN{=}C{=}S \quad (5)$$

wherein R=$C_1$ to $C_6$ alkyl, $C_2$ to $C_6$ substituted alkyl, $C_2$ to $C_{10}$ alkenyl, $C_2$ to $C_{11}$ substituted alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle;
to the solution to form a reaction mixture. The reaction mixture is cooled and filtered to produce III.

Yet another aspect of the invention comprises a method for producing an antimycobacterial compound comprising the formula of:

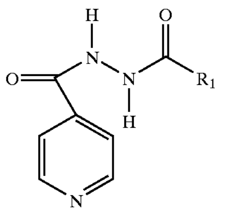
(IV)

wherein $R_1$=$C_1$ to $C_6$ alkyl, $C_2$ to $C_6$ substituted alkyl, $C_2$ to $C_{10}$alkenyl, $C_2$ to $C_{10}$ substituted alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, substituted heterocycle;
which comprises adding diethyl ether to

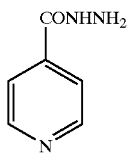
(1)

to produce a solution. The solution is boiled and a carboxylic acid anhydride comprising the formula of:

$$(RCO)_2O \quad (4)$$

wherein R=$C_1$ to $C_6$ alkyl, $C_2$ to $C_6$ substituted alkyl, $C_2$ to $C_{11}$ alkenyl, $C_2$ to $C_{11}$ substituted alkenyl, $C_3$ to $C_7$ cycloalkyl, $C_3$ to $C_7$ substituted cycloalkyl, phenyl, substituted phenyl, $C_7$ to $C_{16}$phenylalkyl, $C_7$ to $C_6$ substituted phenylalkyl, benzyl, substituted benzyl, naphthyl, substituted naphthyl, heterocycle, substituted heterocycle;
is added in ether to the solution to form a reaction mixture. The reaction mixture is refluxed and cooled to produce IV.

Another aspect of this invention involves pharmaceutical compositions comprised of formulas I, II and III.

The pharmaceutical compositions of this invention may be prepared by combining the compounds of Formula I, II and III of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition can be provided by employing conventional techniques. Preferably the composition is in unit dosage form containing an effective amount of the active component, that is, the compounds of Formula I, II and III according to this invention.

The quantity of active component, that is, the compounds of Formula I, II and III do according to this invention, in the pharmaceutical composition and unit dosage form thereof may be varied or adjusted widely depending upon the particular application method, the potency of the particular compound and the desired concentration. Generally, the quantity of active component can range between 20% to 80% by weight of the composition.

BRIEF DESCRIPTION OF THE DRAWING(S)

DESCRIPTION OF THE PREFERRED EMBODIMENT(S)

Figure 1:
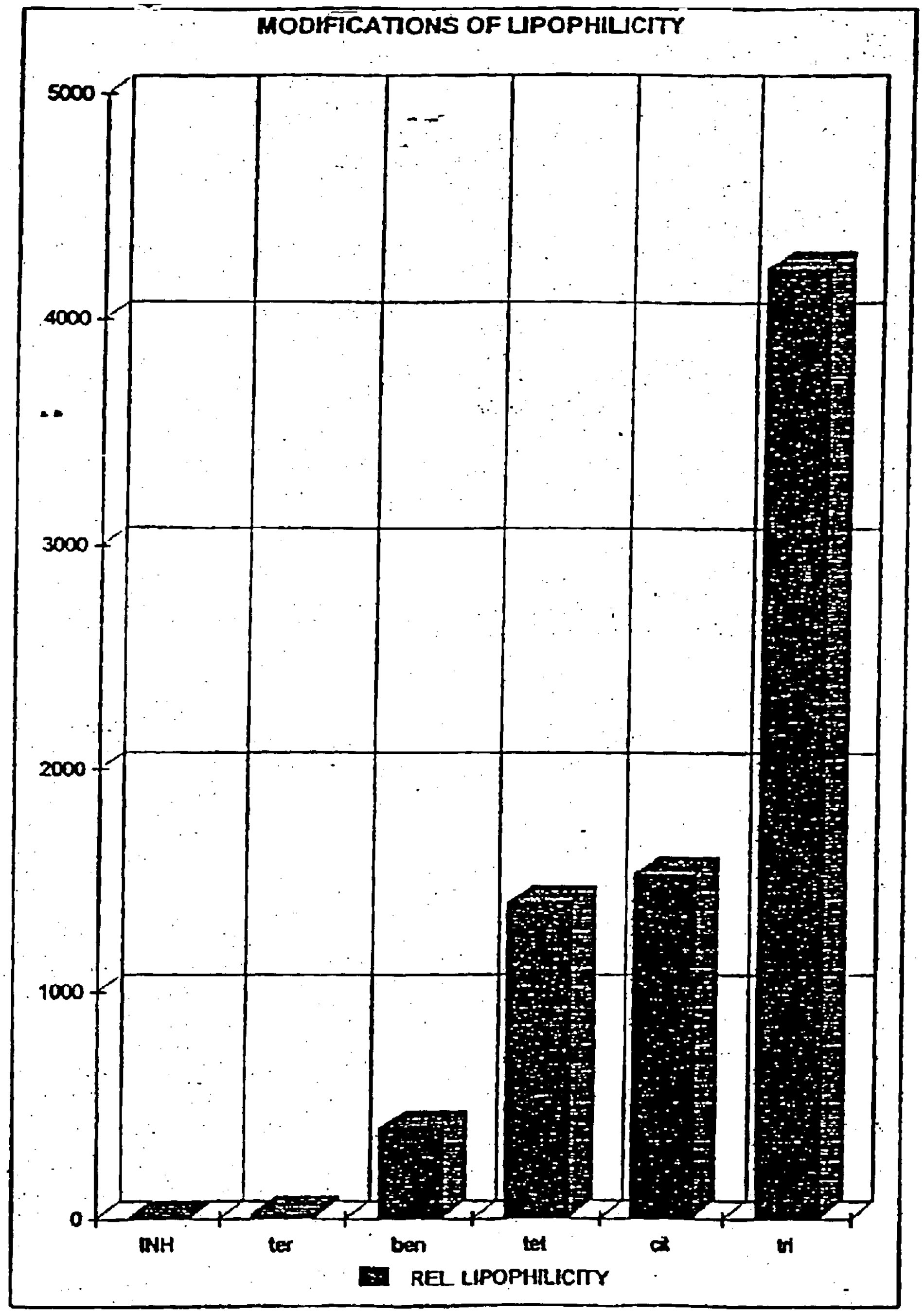
FIG. 1 is bar graph depicting the lipophilicities of INH and isonicotinoylhydrazones of terephthalaldehyde, benzaldehyde, tetradecanal, citronellal and tridecanal.

A general procedure was developed to estimate the relative lipophilicities of compounds by observation of their partitioning between an aqueous solvent and water in biphasic liquid-liquid extraction. As depicted in FIG. 1, the ratio of amounts in each of the respective phases was obtained and compared to the ratio for INH as standard, viz., ratio is set to unity. The compounds of the invention have been prepared with lipophilicities several orders of magnitude greater than that of INH. The advent of a quantitative method for lipophilicity determinations has been particularly important in the examination of the compounds disclosed herein. It is unexpected that the compounds of the invention, such as the Schiff bases and oxadiazolines, have increases in molecular weights by a factor of as much as 2 or more with respect to isoniazid and also have increases in lipophilicities of as much as several orders of magnitude. For example, among the oxadiazolines, where substituent groups $R_1$ or $R_2$ may be aromatics substituted with polarizing functional groups, measured lipophilicities are unexpectedly high. Thus, for the oxadiazoline in which $R_1$=H and $R_2$=3,4-difluorophenyl, the lipophilicity is some three orders of magnitude greater than that of INH, a result which is unexpected.

EXPERIMENTAL PROCEDURES

General Methods and Materials

Elemental analyses were performed by Galbraith Laboratories, Knoxville, Tenn. Melting points (mp) were taken in open capillary tubes using a Mel-Temp apparatus, measured in degrees Centigrade (° C.) and are corrected. Infrared (IR) spectra were recorded on a Perkin-Elmer Model 1600 Fourier transform spectrophotometer as Nujol mulls and are reported in wavenumbers (ν, $cm^{-1}$). Except as specified in the individual procedures, reactants and reagents were obtained from Aldrich Chemical Company and were used as received. Proton nuclear magnetic resonance (NMR) spectra were taken on Bruker 200 or 300 Fourier transform instruments in dimethyl sulfoxide-$d_6$ and are reported in parts per million delta (δ) downfield from internal tetramethylsilane as reference. High resolution mass spectra (HRMS) and low resolution mass spectra were determined at the National Institutes of Health Mass Spectrometry Facility at Michigan State University, East Lansing, Mich. Abbreviations: Standard abbreviations are used for masses in grams (g); volumes in milliliters (mL); quantities in millimoles (mmol); magnetic resonance field strengths in megahertz (Mhz); relative signal strengths in proton NMR (H); proton NMR coupling constants (J) in cycles per second (cps); proton multiplicities as singlets (s), doublets (d), triplets (t) and multiplets (m).

Method for Obtaining Quantitative Estimates of Relative Lipophilicities

A general procedure was devised to estimate relative lipophilicities of the compounds of the invention by observation of their partitioning between an organic phase and water. Thus, to a weighed amount of compound (0.75 mmole) in a flat-bottomed Florence flask containing a stirring bar was delivered by pipet distilled water (5 mL) and also by pipet chloroform (5 mL). The flask was sealed with a cork and paraffin, and the contents were magnetically stirred vigorously for 30 minutes. The cork, paraffin and stirring bar were carefully removed, and the contents of the flask were transferred to a 60 mL separatory funnel. The layers were allowed to stand to achieve good separation. The layers were separated using the separatory funnel. Each layer was individually allowed to evaporate to dryness over night on a pre-weighed watchglass. The ratio of amounts of dry compound remaining after evaporation of the layers on the two watchglasses was obtained (chloroform to water). This ratio was then compared to the same ratio for isoniazid as standard, giving the estimate of relative lipophilicities. The lipophilicity comparison was expressed as $[A_{cmpd}(CHCl_3)/A_{cmpd}(H_2O)$: $A_{inh}(CHCl_3)/A_{inh}(H_2O)]$, where $A_{cmpd}$(solvent) refers to the amount of compound in chloroform or water, as appropriate and $A_{inf}$(solvent) refers to the amount of isonicotinic acid hydrazide in chloroform or water, as appropriate.

Representative examples of the comparisons are provided in FIG. 1 and in the following Chart. Within the Chart, numbers refer to compounds derived from the individual examples of experimental procedures within each family.

Chart. Quantitative Estimates of Relative Lipophilicities of the Compounds of the Invention Compound of Schiff Base Example (Relative Lipophilicity)
43(200)
45(45)
47(316)
48(566)
49(433)
51(400)
52(189)

Compound of Oxadiazoline Example (Relative Lipophilicity)
4(35,667)
8(1333)
9(1426)
10(3080)

General Structural Outline for Schiff Base Synthesis

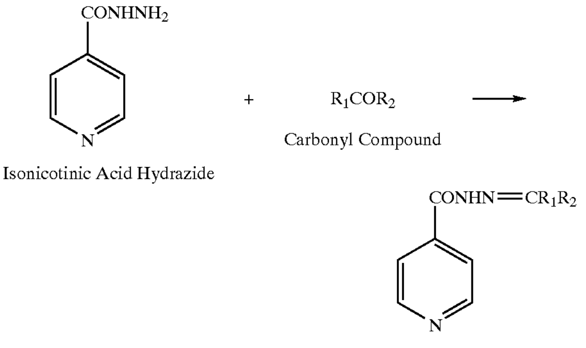

Isonicotinic Acid Hydrazide

Carbonyl Compound

Schiff Base

This section describes the general considerations for the synthesis of Schiff bases. The Schiff bases are prepared by the reactions of isonicotinic acid hydrazide with carbonyl compounds in an appropriate solvent. Reaction conditions and solvent choices are critical to insure that the products of the syntheses are isolated in useful form.

The biological evaluation of compounds prepared for the purposes of drug design and drug discovery requires that materials be readily available in pure form on quantity scale, generally understood to be gram or multi-gram scale, as opposed to milligram scale. Gram scale quantities are necessary for the large numbers of biological tests which must be performed and replicated for the evaluation of a new drug candidate.

Products of synthetic reactions are most desirable when they can be easily and cheaply obtained as dry and free-flowing solids. In the long run, dry and free-flowing solids permit better formulations of drugs as tablets, capsules or syrups. The method of Schiff base synthesis disclosed herein yields products directly as dry free-flowing solids in analytically pure form. The prior art synthesis yields products that are obtained as intractable oils, difficult and labor-intensive to purify or bring into dry free-flowing form. The products of synthesis disclosed herein are suitable for biological evaluation or for further chemical transformation to other Schiff base congeners.

It is within the scope of the invention that the method of the Schiff base synthesis allows the economical use of solvents. The method of Schiff base synthesis conserves the use of solvents. The solvents, disclosed herein, which are required are inexpensive and may be conveniently recycled, if desired, by the use of a technique described below.

Isonicotinic acid hydrazide is used as received directly and inexpensively in greater than 95% purity from such commercial sources as Fluka A.-G., Lancaster or Aldrich Chemical Companies, all of which can supply this material in pure form in bulk quantities. Purity is confirmed by analysis using melting point, infrared, near infrared and magnetic resonance spectroscopy.

A 0.4 Molar solution is prepared of isonicotinic acid hydrazide in absolute ethanol, at reflux. The ethanol is used as received from Pharmco, Incorporated. The preparation of the solution at reflux is done by mixing the required weight of isonicotinic acid hydrazide with the necessary volume of absolute ethanol in a standard taper round bottom flask fitted for reflux with a temperature-controlled heating mantle, carborundum boiling chip and condenser. The volume of the flask is chosen in such a way that the contents of the entire reaction mixture do not exceed 50% of the flask's nominal capacity.

At room temperature, much of the isonicotinic acid hydrazide does not dissolve. The mixture of isonicotinic acid hydrazide and ethanol is brought to the boil and forms a clear colorless solution. The appearance of pronounced yellow color or pink tinge in the boiling mixture is unacceptable and generally indicates impure isonicotinic acid hydrazide. This impurity will lead to an unsatisfactory product from the viewpoint of quality and dry free-flowing form.

To the clear colorless solution at reflux is added dropwise through the top of the condenser the requisite carbonyl compound as a 5 Molar solution in absolute ethanol. The rate of addition is such that boiling does not cease during the addition. In the refluxing reaction mixture, the weights of carbonyl compound and isonicotinic acid hydrazide will have been chosen such that the compounds will be in a ratio by moles of about 1.67 to 1.00.

After the complete addition of the 5 Molar solution of the carbonyl compound, refluxing is continued for 1.5 hours. Heating is stopped and the clear colorless reaction mixture is allowed to cool and stand for 24 hours.

The condenser is removed from the round bottom flask, and the flask is fitted with a Dean-Stark apparatus to ensure convenient distillation and recovery of solvent for recycling. A new carborundum boiling chip is added, and the reaction mixture is brought to the boil. Ethanol is distilled out of the reaction mixture using the Dean-Stark apparatus. The ethanol may thus be recovered and recycled for further use.

Removal of ethanol by distillation continues until the reaction mixture in the round bottom flask has been reduced to half volume. The reaction mixture is allowed to cool to room temperature and the round bottom flask is removed from the Dean-Stark apparatus.

The volume of the reaction mixture is noted. An equivalent volume of diethyl ether (EM Science absolute grade) is added. The mixture is swirled and permitted to stand. Solid begins to form in the solution and continues to form over night.

The solid is filtered off by gravity using Whatman No. 1 filter paper and allowed to dry on the filter cake. The dry free-flowing solid product thus obtained is then analyzed and characterized by the usual means, including melting point, infrared, near infrared, mass and magnetic resonance spectroscopy and elemental analysis.

EXPERIMENTAL PROCEDURES—SCHIFF BASES

Example 1

Isonicotinoylhydrazone of Crotonaldehyde

This compound was prepared from crotonaldehyde and isonicotinic acid hydrazide using the General Structural Outline for Schiff Base Synthesis. 73% of the isonicotinoylhydrazone of crotonaldehyde, melting point 198–201° C.; IR ν 3178, 1664, 1638, 1604, 1579, 1414, 1300, 1218, 1150, 1096, 1065, 1047, 998, 983, 930, 897, 847 $cm^1$; NMR (300 megahertz) δ 11.8 (relative signal strength 1H, multiplicity singlet). 8.8 (2H, d, coupling constant J=6 cycles per second), 8.1 (1H, br d, J=6 cps), 7.8 (2H, d, J=6 cps), 6.25 (2H, m), 1.9 (3H, br d); high resolution mass spectrum (FAB method) m/z 190.0983 (M+H) ($C_{10}H_{11}N_3O$+H requires 190.0980) was obtained.

Analysis. Calculated for $C_{10}H_{11}N_3O$: C, 63.48; H, 5.86. Found: C, 63.79; H, 5.94.

Example 2

Isonicotinoylhydrazone of trans-2-Pentenal

This compound was prepared from trans-2-pentenal and isonicotinic acid hydrazide using the General Structural Outline for Schiff Base Synthesis. 54% of the isonicotinoylhydrazone of trans-2-pentenal, melting point 161–164° C.; IR ν 3238, 1654, 1639, 1582, 1546, 1407, 1293, 1250, 1214, 1192, 1146, 1066, 1049, 1018, 1001, 957, 909, 840, 756, 722 $cm^{-1}$; NMR (300 megahertz) δ 11.8 (11H, br s), 8.8 (2H, d, J=6 cps), 8.1 (1H, d, J=6 cps), 7.8 (2H, d, J=6 cps), 6.25 (2H, m), 2.3 (2H, m), 1.0 (3H, t, J=6 cps); high resolution mass spectrum (FAB method) m/z 204.1139 (M+H) ($C_{11}H_{13}N_3O$+H requires 204.1137) was obtained.

Analysis. Calculated for $C_{11}H_{13}N_3O$: C, 65.01; H, 6.45. Found: C, 65.18; H, 6.42.

Example 3

Isonicotinoylhydrazone of trans-2-Hexenal

From trans-2-hexenal, 30% of the isonicotinoylhydrazone of trans-2-hexenal, melting point 152–154° C.; IR ν 3224, 1654, 1639, 1596, 1582, 1546, 1406, 1300, 1212, 1191, 1152, 1067, 1041, 994, 956, 909, 838, 755, 722 $cm^{-1}$; NMR (300 megahertz) δ 11.8 (1H, br s), 8.8 (2H, d, J=6 cps), 8.1 (1H, br d, J=6 cps), 7.8 (2H, d, J=6 cps), 6.25 (2H, m), 2.2 (2H, m), 1.45 (2H, sextet, J=6 cps), 0.9 (3H, t, J=6 cps); high resolution mass spectrum (FAB method) m/z 218.1284 (M+H) ($C_{12}H_{15}N_3O$+H requires 218.1293) was obtained.

Analysis. Calculated for $C_{12}H_{15}N_3O$: C, 66.34; H, 6.96. Found: C, 66.33; H, 7.13.

Example 4

Isonicotinoylhydrazone of trans-2-Heptenal

From trans-2-heptenal, 35% of the isonicotinoylhydrazone of trans-2-heptenal, melting point 152–154° C.; IR ν 3246, 1656, 1633, 1595, 1582, 1546, 1420, 1407, 1331, 1297, 1236, 1213, 1148, 1068, 1034, 1006, 9.62, 939, 903, 876, 840, 754, 721 $cm^{-1}$; NMR (300 megahertz) δ 11.8 (1H, br s), 8.8 (2H, d, J=6 cps), 8.1 (1H, br d, J=6 cps), 7.8 (2H, d, J=6 cps), 6.28 (2H, m), 2.2 (2H, m), 1.38 (4H, m), 0.9 (3H, t, J=6 cps); high resolution mass spectrum (FAB method) m/z 232.1443 (M+H) ($Cl_3H_{17}N_3O$+H requires 232.1450) was obtained.

Analysis. Calculated for $C_{13}H_{17}N_3O$: C, 67.51; H, 7.41. Found: C, 67.38; H, 7.53.

Example 5

Isonicotinoylhydrazone of trans-2-Methyl-2-Butenal

From trans-2-methyl-2-butenal, 78% of the isonicotinoylhydrazone of trans-2-methyl-2-butenal, melting point 189–191° C.; IR ν 3195, 1666, 1634, 1601, 1575, 1547, 1410, 1300, 1217, 1159, 1064, 1025, 996, 952, 848, 825, 724 $cm^{-1}$; NMR (300 megahertz) δ 11.7 (1H, br s), 8.8 (2H, d, J=6 cps), 8.1 (1H, s), 7.8 (2H, d, J=6 cps), 6.0 (1H, m), 1.9 (6H, m); high resolution mass spectrum (FAB method) m/z 204.1144 (M+H) ($C_{11}H_{13}N_3O$+H requires 204.1137) was obtained.

Analysis. Calculated for $C_{11}H_{13}N_3O$: C, 65.01; H, 6.45. Found: C, 65.04; H, 6.56.

Example 6

Isonicotinoylhydrazone of Citral

This compound was prepared from citral and isonicotinic acid hydrazide using the General Structural Outline for Schiff Base Synthesis. 590/o of the isonicotinoylhydrazone of citral, melting point 124–125° C.; IR ν 3178, 3029, 1638, 1595, 1574, 1548, 1412, 1328, 1297, 1216, 1199, 1139, 1068, 1044, 989, 961, 907, 868, 849, 822, 761, 723 $cm^{-1}$ was obtained.

Analysis. Calculated for $C_{16}H_{21}N_3O$: C, 70.82; H, 7.80. Found: C, 70.78; H, 7.89.

Example 7

Di-isonicotinoylhydrazone of Glyoxal

This compound was prepared from glyoxal and isonicotinic acid hydrazide (2 equivalents) using the General Structural Outline for Schiff Base Synthesis. 90% of the di-isonicotinoylhydrazone of glyoxal, melting point >305° C.; IR ν 3198, 3052, 1666, 1579, 1535, 1407, 1310, 1288, 1213, 1156, 1063, 963, 915, 842, 763, 730 $cm^{-1}$ was obtained.

Analysis. Calculated for $C_{14}H_{12}N_6O_2$: C, 56.75; H, 4.08. Found: C, 56.85; H, 4.10.

Example 8

Isonicotinoylhydrazone of Ethyl Butyryl Acetate

This compound was prepared from ethyl butyryl acetate and isonicotinic acid hydrazide using the General Structural Outline for Schiff Base Synthesis. 98% of the isonicotinoylhydrazone of ethyl butyryl acetate, melting point 89–90° C.; IR ν 3163, 1733, 1675, 1655, 1627, 1599, 1558, 1548, 1426, 1406, 1336, 1298, 1261, 1196, 1162, 1095, 1044, 1030, 992, 974, 918, 886, 842, 762, 722 $cm^{-1}$ was obtained.

Analysis. Calculated for $C_{14}H_{19}N_3O_3$: C, 60.64; H, 6.91. Found: C, 60.26; H, 7.02.

Example 9

Isonicotinoylhydrazone of Ethyl Acetoacetate

This compound was prepared from ethyl acetoacetate and isonicotinic acid hydrazide using the General Structural Outline for Schiff Base Synthesis. 85% of the isonicotinoylhydrazone of ethyl acetoacetate, melting point 99° C.; IR ν 3200, 1733, 1690, 1655, 1635, 1598, 1554, 1535, 1406, 1336, 1301, 1268, 1182, 1142, 1067, 1037, 840, 756, 721, 672 $cm^{-1}$ was obtained.

Analysis. Calculated for $C_{12}H_{15}N_3O_3$: C, 57.82; H, 6.07. Found: C, 57.88; H, 6.26.

Example 10

Isonicotinoylhydrazone of Citronellal

This compound was prepared from citronellal and isonicotinic acid hydrazide using the General Structural Outline for Schiff Base Synthesis. 29% of the isonicotinoylhydrazone of citronellal, melting point 78–80° C.; IR ν 3226, 1651, 1619, 1596, 1544, 1410, 1297, 1215, 1135, 1067, 1032, 975, 906, 844, 757, 722 $cm^{-1}$ was obtained.

Analysis. Calculated for $C_{16}H_{23}N_3O$: C, 70.30; H, 8.48. Found: C, 70.35; H, 8.78.

Example 11

Di-isonicotinoylhydrazone of Terephthalaldehyde

This compound was prepared from terephthalaldehyde and isonicotinic acid hydrazide (2 equivalents) using the General Structural Outline for Schiff Base Synthesis. 90% of the di-N isonicotinoylhydrazone of terephthalaldehyde, melting point >300° C.; IR ν 3246, 3067, 1653, 1600, 1543, 1507, 1408, 1293, 1215, 1154, 1107, 1068, 969, 923, 839, 812, 755, 719 $cm^{-1}$ was obtained.

Analysis. Calculated for $C_{20}H_{16}N_6O_2$: C, 64.51; H, 4.33. Found: C, 64.59; H, 4.44.

Example 12

Isonicotinoylhydrazone of 4-Butoxybenzaldehyde

This compound was prepared from 4-butoxybenzaldehyde and isonicotinic acid hydrazide using the General Structural Outline for Schiff Base Synthesis. 91% of the isonicotinoylhydrazone of 4-butoxybenzaldehyde, melting point 148–149° C.; IR ν 3272, 1650, 1260 $cm^{-1.}$ Analysis. Calculated for $C_{17}H_{19}N_3O_2$: C, 68.68; H, 6.44. Found: C, 68.84; H, 6.61.

Example 13

Isonicotinoylhydrazone of Tridecanal.

This compound was prepared from tridecanal and isonicotinic acid hydrazide using the General Structural Outline for Schiff Base Synthesis. 73% of the isonicotinoylhydrazone of tridecanal, melting point 92–93° C.; IR ν 3260, 3066, 1654, 1624, 1597, 1548, 1412, 1294, 1041, 846, 754, 727 $cm^{-1}$ was obtained.

Analysis. Calculated for $C_{19}H_{31}N_3O$: C, 71.88; H, 9.84. Found: C, 71.68; H, 10.14.

Example 14

Isonicotinoylhydrazone of Perillaldehyde

This compound was prepared from perillaldehyde and isonicotinic acid hydrazide using the General Structural Outline for Schiff Base Synthesis. 98% of the isonicotinoylhydrazone of perillaldehyde, melting point 86–88° C.; IR ν 3464, 3192, 1667, 1636, 1604, 1585, 1562, 1532, 1410, 1290, 1235, 1185, 1140, 1062, 1042, 1006, 971, 942, 910, 888, 847, 754, 722 $cm^{-1}$ was obtained.

Analysis. Calculated for $C_{16}H_{19}N_3O{\times}1.5H_2O$: C, 64.84; H, 7.48. Found: C, 64.75; H, 7.60.

Example 15

Isonicotinoylhydrazone of 4-Nitrobenzaldehyde

This compound was prepared from 4-nitrobenzaldehyde and isonicotinic acid hydrazide using the General Structural Outline for Schiff Base Synthesis. 96% of the isonicotinoylhydrazone of 4-nitrobenzaldehyde, melting point 279–280° C., lit mp 270–271° C. [Shchukina et al., *Doklady Akad. Nauk S.S.S.R.,* 84, 981–984 (1952); *Chem. Abstr.,* 46, 10431 i (1952)], lit mp 273–274° C. [Fenech et al., *Farmaco, Ed. Sci.,* 13, 681 (1958)] was obtained.

Example 16

Isonicotinoylhydrazone of Cyclohexanone

This compound was prepared from cyclohexanone in 81% yield, mp 167–168° C., lit mp 162–163° C. [Shchukina et al., *Doklady Akad. Nauk S.S.S.R.,* 84, 981–984 (1952); *Chem. Abstr.,* 46, 10431 i (11952)]; IR ν 3212, 1662, 1637, 1597, 1528, 1406, 1302, 1285, 1245, 1214, 1139, 1036, 839, 755, 722 $cm^{-1}$; NMR (300 megahertz) δ 10.8 (1H, br s), 8.7 (2H, d, J=6 cps), 7.6 (2H, d, J=6 cps), 2.4 (4H, m), 1.6 (4H, m).

Analysis. Calculated for $C_{12}H_{15}N_3O$: C, 66.32; H, 6.97. Found: C, 65.90; H, 6.90.

This material was further characterized by its exchange reaction with benzaldehyde to produce the isonicotinoylhydrazone of benzaldehyde, in a procedure devised for this application. Thus the isonicotinoylhydrazone of cyclohexanone (0.82 g) was weighed into a 50 mL pear-shaped flask and brought to reflux with absolute ethanol (15 mL). To this mixture was added benzaldehyde (0.69 g) at such a rate that vigorous boiling continued throughout the addition. The aldehyde was washed in with a further portion of ethanol (3 mL), all at the boil. Refluxing was continued for one hour. The mixture was allowed to cool to room temperature and ether (35 mL) added. Over night a solid formed (90%), which was identical (band-for-band comparison of infrared spectra) to an authentic specimen of the isonicotinoylhydrazone of benzaldehyde, independently prepared from isonicotinic acid hydrazide and benzaldehyde according to the procedure specified for Example 18.

Example 17

Isonicotinoylhydrazone of Acetone.

This compound was prepared from acetone and isonicotinic acid hydrazide using the General Structural Outline for Schiff Base Synthesis. 48% of the isonicotinoylhydrazone of acetone, melting point 161–162° C.; IR ν 3184, 1654, 1633, 1534, 1297, 1266, 1208, 1148, 1062, 1028, 989, 914, 836 $cm^{-1}$; NMR (300 megahertz) δ 10.8 (11H, br s), 8.7 (2H, d, J=6 cps), 7.7 (2H, d, J=6 cps), 2.0 (3H, s), 1.9 (3H, s).

Analysis. Calculated for $C_9H_{11}N_3O$: C, 61.00; H, 6.25. Found: C, 60.95; H. 6.21.

This material was further characterized by its exchange reaction with 2,4-dinitrophenylhydrazine to produce the 2,4-dinitrophenylhydrazine of acetone, in a reaction procedure devised as part of this work. Thus the isonicotinoylhydrazone of acetone (0.135 g) was dissolved in the minimum volume (5 mL) of absolute ethanol in a 50 mL conical flask. To this solution was then added standard 2,4-dinitrophenylhydrazine reagent (10 mL, prepared according to A. Vogel, *Text-book of Practical Organic Chemistry,* 1966, p. 1061) at room temperature. Formation of a yellow precipitate was instantaneous. The mixture was warmed on a hot plate to just below the boiling point and swirled continuously. The mixture was then cooled by holding the outside of the reaction flask in a stream of cold tap water. The resulting yellow-orange 2,4-dinitrophenylhydrazone of acetone (72%) was allowed to stand for a few hours, then filtered off by gravity, mp 127–128° C. (from ethanol); mixed mp with an authentic specimen (prepared directly from acetone and 2,4-dinitrophenylhydrazine according to the method of Vogel cited above) 127–128° C.; lit mp 128° C. [A. Vogel, *Text-book of Practical Organic Chemistry,* 1966, pp. 334, 346, 723, 743; Behforouz, et al., *J. Org. Chem.,* 50, 1186 (1985)].

Example 18

Isonicotinoylhydrazone of Benzaldehyde

This compound was prepared from benzaldehyde and isonicotinic acid hydrazide using the General Structural Outline for Schiff Base Synthesis. 98% of the isonicotinoylhydrazone of benzaldehyde, melting point 197° C., lit mp 194–195° C. [P. Stecher, editor, The Merck Index, Rahway, N.J., Merck and Company, 1968, p. 587 and Fenech et al., *Farmaco, Ed. Sci.,* 13, 681 (1958)]; IR ν 3192, 1691, 1598, 1565, 1412, 1354, 1284, 1150, 1081, 1058, 998, 952, 920, 845, 767, 724 $cm^{-1}$.

This material was further characterized by its exchange reaction with 2,4-dinitrophenylhydrazine to produce the 2,4-dinitrophenylhydrazone of benzaldehyde, in a reaction procedure devised as part of this work. Thus the isonicotinoylhydrazone of benzaldehyde (0.153 g) was dissolved with warming in the minimum volume (ca. 5 mL) of absolute ethanol in a 50 mL conical flask. To this solution was then added standard 2,4-dinitrophenylhydrazine reagent (10 mL, prepared according to A. Vogel, *Text-book of Practical Organic Chemistry,* 1966, p. 1061) at room temperature. Formation of a fluorescent yellow-orange precipitate was immediate. The resulting yellow-orange 2,4-dinitrophenylhydrazone of benzaldehyde (91%) was filtered off by gravity, mp 231–234° C., lit mp 237° C. [A. Vogel, *Text-book of Practical Organic Chemistry,* 1966, pp. 334, 346, 723, 743; Behforouz et al., *J. Org. Chem.,* 50, 1186 (1985)].

Example 19

Isonicotinoylhydrazone of Salicylaldehyde

This compound was prepared from salicylaldehyde and isonicotinic acid hydrazide, obtaining 83% of the isonicotinoylhydrazone of salicylaldehyde, melting point 247–250° C., lit mp 232–233° C. and 251° C. [P. Stecher, editor, The Merck Index, Rahway, N.J., Merck and Company, 1968, p. 587], lit mp 238–239° C. [Shchukina et al., *Doklady Akad. Nauk S.S.S.R.,* 84, 981–984 (1952); *Chem. Abstr.,* 46, 10431 i (1952)], lit mp 251° C. [Buu-Hoi et al., *J. Chem. Soc.,* 1358 (1953)], lit mp 243–245° C. [Fenech et al., *Farmaco, Ed. Sci.,* 13, 681 (1958)], lit mp 243° C. [Penkert, *Arzneimittel Forsch.,* 7, 304 (1957)]; IR ν 3180, 1682, 1624, 1611, 1567, 1553, 1408, 1290, 1274, 1233, 1208, 1159, 1067, 1034, 999, 872, 850, 772, 752, 688 $cm^{-1}$.

This material was further characterized by its exchange reaction with 2,4-dinitrophenylhydrazine to produce the 2,4-dinitrophenylhydrazone of salicylaldehyde, in a reaction procedure devised as part of this work. Thus the isonicotinoylhydrazone of salicylaldehyde (0.150 g) was mixed with warming with 5 mL of absolute ethanol in a 50 mL conical flask. Not all the solid dissolved. The fluid portion of the mixture was drawn off with a Pasteur pipet and added directly to standard 2,4-dinitrophenylhydrazine reagent (10 mL, prepared according to A. Vogel, *Text-book of Practical Organic Chemistry,* 1966, p. 1061) at room temperature. Formation of a fluorescent orange precipitate was immediate. The resulting, orange 2,4-dinitrophenylhydrazone of salicylaldehyde (17%) was filtered off by gravity, mp 248–250° C., lit mp 252° C. [A. Vogel, *Text-book of Practical Organic Chemistry,* 1966, pp. 334, 346, 723, 743; Behforouz et al., *J. Org. Chem.,* 50, 1186(1985)].

Example 20

Isonicotinoylhydrazone of Vanillin

This compound was prepared from vanillin and isonicotinic acid hydrazide, yielding 92% of the isonicotinoylhydrazone of vanillin, melting point 226–227° C., lit mp 219–220° C. [Shchukina et al., *Doklady Akad. Nauk S. S. R.,* 84, 981–984 (1952); *Chem. Abstr.,* 46, 10431 i (1952)]; IR ν 3190, 1651 $cm^{-1}$.

EXAMPLE 21

Isonicotinoylhydrazone of para-Anisaldehyde

This compound was prepared from para-anisaldehyde and isonicotinic acid hydrazide using the General Structural Outline for Schiff Base Synthesis. 92% of the isonicotinoylhydrazone of para-anisaldehyde, melting point 137–139° C., lit mp 126–127° C. [Shchukina et al., *Doklady Akad. Nauk S.S.S.R.,* 84, 981–984 (1952); *Chem. Abstr.,* 46, 10431 i (1952)], lit mp 172–174° C. [Fox et al., *J. Org. Chem.,* 18, 983 (1953)]; IR ν 34364, 1655 $cm^{-1}$; NMR (200 megahertz) δ 12.0 (1H, br s), 8.8 (2H, d, J=6 cps), 8.4 (1H, s), 7.8 (2H, d, J=6 cps), 7.7 (2H, d, J=6 cps), 7.0 (2H, d, J=6 cps), 3.9 (3H, s).

This material was further characterized by its qualitative exchange reaction with 2,4-dinitrophenylhydrazine to produce the 2,4-dinitrophenylhydrazone of para-anisaldehyde, in a reaction procedure devised as part of this work. Thus the isonicotinoylhydrazone of para-anisaldehyde (0.250 g) was dissolved in the minimum volume (5 mL) of absolute ethanol in a 50 mL conical flask. The material dissolved readily without heating. To this solution was then added standard 2,4-dinitrophenylhydrazine reagent (10 mL, prepared according to A. Vogel, *Text-book of Practical Organic Chemistry*, New York, John Wiley and Sons, 1966, p. 1061) at room temperature. Formation of a bright orange precipitate was immediate. The resulting orange 2,4-dinitrophenylhydrazone of para-anisaldehyde was allowed to stand for a few hours, then filtered off by gravity, mp 249–252° C. (from ethanol); lit mp 252° C. [A. Vogel, *Text-book of Practical Organic Chemistry*, New York, John Wiley and Sons, 1966, pp. 334, 346, 723, 743; see also M. Behforouz, J. Bolan and M. Flynt, *J. Org. Chem.,* 50, 1186 (1985)].

Example 22

Isonicotinoylhydrazone of meta-Anisaldehyde.

This compound was prepared using the General Structural Outline for Schiff Base Synthesis. 90% yield of the isonicotinoylhydrazone of meta-anisaldehyde, mp 199° C.; IR ν 3195, 1643 $cm^{-1}$; NMR (200 megahertz) δ 12.1 (1H, br s), 8.9 (2H, d, J=6 cps), 8.4 (1H, s), 7.8 (2H, d, J=6 cps), 7.4–7.0 (3H, m), 3.9 (3H, s) was obtained.

Example 23

Isonicotinoylhydrazone of Methyl Jasmonate

This compound was prepared using the General Structural Outline for Schiff Base Synthesis. 67% yield of the isonicotinoylhydrazone of methyl jasmonate, mp 90–91° C.; IR ν 3271, 1740, 1664, 1644, 1554, 1527, 1403, 1300, 1283, 1264, 1201, 1158, 1126, 1061, 1036, 840, 754, 722 $cm^{-1}$ was obtained.

Analysis. Calculated for $C_{19}H_{25}N_3O_3 \times H_2O$: C, 63.94; H, 7.48. Found: C, 64.30; H, 7.07.

Example 24

Isonicotinoylhydrazone of Decanal

This compound was prepared from isonicotinic acid hydrazide and decyl aldehyde, giving a 93% yield of the isonicotinoylhydrazone of decanal, mp 83–85° C.; IR ν 3252, 1655, 1624, 1597, 1548, 1411, 1324, 1297, 1248, 1220, 1158, 1066, 1036, 964, 935, 891, 876, 846, 754, 728 $cm^{-1}$.

Analysis. Calculated for $C_{16}H_{25}N_3O$: C, 69.78; H, 9.15. Found: C, 69.82; H, 9.67.

Example 25

Isonicotinoylhydrazone of Tetradecanal

This compound was prepared from isonicotinic acid hydrazide and tetradecanal, giving a 73% yield of the isonicotinoylhydrazone of tetradecanal, mp 89–91° C.; IR ν 3258, 1654, 1624, 1553, 1410, 1295, 1221, 1158, 1120, 1099, 1065, 1042, 962, 846, 753, 718 $cm^{-1}$.

Analysis. Calculated for $C_{20}H_{33}N_3O$: C, 72.46; H, 10.04. Found: C, 72.20; H, 10.33.

Example 26

Isonicotinoylhydrazone of ortho-Anisaldehyde

This compound was prepared from isonicotinic acid hydrazide and ortho-anisaldehyde, giving a 78% yield of the isonicotinoylhydrazone of ortho-anisaldehyde, mp 194–195° C., lit mp 219–220° C. [H. Fujiwara, *Yakugaku Zasshi,* 78, 1034 (1958) and 1045 (1958)]; IR ν 3191, 1652, 1602, 1578, 1558, 1551, 1439, 1406, 1304, 1256, 1163, 1064, 1045, 1024, 961, 929, 851, 836, 753, 686 $cm^{-1}$.

Example 27

Isonicotinoylhydrazone of trans-alpha-Methylcinnamaldehyde

This compound was prepared from isonicotinic acid hydrazide and trans-alpha-methylcinnamaldehyde, giving a 76% yield of the isonicotinoylhydrazone of trans-alpha-methylcinnamaldehyde as a sticky solid; IR ν 3187, 1651, 1622, 1598, 1579, 1551, 1404, 1309, 1212, 1075, 1016, 967, 935, 841, 749, 723, 697 $cm^{-1}$.

Analysis. Calculated for $C_{16}H_{15}N_3O$: C, 72.43; H, 5.70. Found: C, 72.19; H, 5.67.

Example 28

Isonicotinoylhydrazone of 4-Fluorobenzaldehyde

This compound was prepared from isonicotinic acid hydrazide and 4-fluorobenzaldehyde according to the General Structural Outline for Schiff Base Synthesis, giving a 76% yield of the isonicotinoylhydrazone of 4-fluorobenzaldehyde as a white solid, mp 187–189° C.; IR ν 3469, 3257, 1656, 1599, 1562, 1551, 1509, 1408, 1302, 1232, 1156, 1064, 1003, 840, 789, 752 $cm^{-1}$.

Analysis. Calculated for $C_{13}H_{10}N_3OF \times H_2O$: C, 59.76; H, 4.63. Found: C, 59.68; H, 4.68.

Example 29

Isonicotinoylhydrazone of Cyclopentanone

This compound was prepared from isonicotinic acid hydrazide and cyclopentanone according to the General Structural Outline for Schiff Base Synthesis, giving a 53% yield of the isonicotinoylhydrazone of cyclopentanone as a white solid, mp 177° C., IR ν 3197, 1655, 1596, 1534, 1414, 1405, 1291, 1210, 1168, 1140, 1064, 1041, 992, 925, 840, 762, 754, 722 $cm^{-1}$.

This material was characterized on the basis of its exchange reaction with benzaldehyde to produce the isonicotinoylhydrazone of benzaldehyde, in a procedure devised for this application. Thus the isonicotinoylhydrazone of cyclopentanone (0.73 g) was weighed into a 50 mL pear-shaped flask and brought to reflux with absolute ethanol (12 mL). To this mixture was added benzaldehyde (0.64 g) at such a rate that vigorous boiling continued throughout the addition. The aldehyde was washed in with a further portion of ethanol (3 mL), all at the boil. Refluxing was continued for one hour. The mixture was allowed to cool to room temperature and ether (35 mL) added. Over night a solid formed (48%), which was identical (band-for-band comparison of infrared spectra) to an authentic specimen of the isonicotinoylhydrazone of benzaldehyde, independently prepared from isonicotinic acid hydrazide and benzaldehyde according to the procedure specified for Example 18.

Example 30

Isonicotinoylhydrazone of 4-tertiary-Butylcyclohexanone

This compound was prepared from isonicotinic acid hydrazide and 4-tertiary-4-butylcyclohexanone according to the General Structural Outline for Schiff Base Synthesis, giving a 82% yield of the isonicotinoylhydrazone of tertiary-butylcyclohexanone as a white solid, mp 152° C., IR ν 3197, 1655, 1596, 1534, 1414, 1405, 1291, 1210, 1168, 1140, 1064, 1041, 992, 925, 840, 762, 754, 722 $cm^{-1}$.

EXAMPLE 31

Isonicotinoylhydrazone of Cycloheptanone

This compound was prepared from isonicotinic acid hydrazide and cycloheptanone according to the General Structural Outline for Schiff Base Synthesis, giving a 60% yield of the isonicotinoylhydrazone of cycloheptanone as a white solid, mp 123° C., IR ν 3197, 1655, 1596, 1534, 1414, 1405, 1291, 1210, 1168, 1140, 1064, 1041, 992, 925, 840, 762, 754, 722 $cm^{-1}$.

Example 32

Di-isonicotinoylhydrazone of 1,4-Cyclohexanedione.

This compound was prepared from isonicotinic acid hydrazide (2 equivalents) and 1,4-cyclohexanedione according to the General Structural Outline for Schiff Base Synthesis, giving a 99% yield of the di-isonicotinoylhydrazone of 1,4-cyclohexanedione as a white solid, mp 177° C. (dec), IR ν 3262, 1714, 1649, 1633, 1596, 1552, 1520, 1492, 1416, 1306, 1292, 1281, 1215, 1142, 1070, 1043, 992, 842, 756, 726 $cm^{-1}$.

Example 33

Isonicotinoylhydrazone of 3,3,5-Trimethylcyclohexanone

This compound was prepared using the General Structural Outline for Schiff Base Synthesis. One thus obtained a 76% yield of the isonicotinoylhydrazone of 3,3,5-trimethylcyclohexanone, mp 149–151° C.; IR ν 3174, 1650, 1628, 1598, 1552, 1533, 1409, 1339, 1293, 1227, 1164, 1139, 1068, 1032, 842, 760, 722 $cm^{-1}$.

Analysis. Calculated for $C_{15}H_{21}N_3O$: C, 69.47; H, 8.16. Found: C, 69.42; H, 8.17.

Example 34

Isonicotinoylhydrazone of 2-Fluoro-4-Methoxybenzaldehyde

This compound was prepared using the General Structural Outline for Schiff Base Synthesis. 70% yield of the isonicotinoylhydrazone of 2-fluoro-4-methoxybenzaldehyde, mp, 128–132° C. (uncorr); IR ν 3452, 3150, 1657, 1622, 1598, 1592, 1549, 1505, 1412, 1333, 1260, 1248, 1224, 1198, 1154, 1053, 1023, 960, 937, 919, 838, 728, 725 $cm^{-1}$ was obtained.

Analysis. Calculated for $C_{14}H_{12}N_3O_2F{\times}H_2O$: C, 57.73; H, 4.84. Found: C, 57.56; H, 4.90.

Example 35

Isonicotinoylhydrazone of 6-Methoxy-2-naphthaldehyde

This compound was prepared in 93% yield from the reaction of isonicotinic acid hydrazide and 6-methoxy-2-naphthaldehyde, mp 198–199° C. (uncorr), IR ν 3213, 1658, 1625, 1594, 1550, 1408, 1295, 1273, 1248, 1196, 1187, 1144, 1051, 1030, 958, 941, 867, 844, 813, 749, 720 $cm^{-1}$.

Example 36

Isonicotinoylhydrazone of 3-Methoxy-4,5-methylenedioxybenzaldehyde

This compound was prepared in 76% yield from the reaction of isonicotinic acid hydrazide and 3-methoxy-4,5-methylenedioxybenzaldehyde, mp 190–191° C. (uncorr), IR ν 3203, 1652, 1590, 1546, 1505, 1406, 1313, 1299, 1200, 1166, 1133, 1091, 1064, 1039, 992, 950, 926, 907, 842, 823, 753, 738, 721 $cm^{-1}$.

Example 37

Isonicotinoylhydrazone 4-methoxy-1-naphthaldehyde

This compound was prepared in 89% yield from the reaction of isonicotinic acid hydrazide and 4-methoxy-1-naphthaldehyde, mp 238–239° C. (uncorr), IR ν 3172, 1677, 1603, 1573, 1555, 1510, 1407, 1322, 1294, 1246, 1227, 1173, 1147, 1092, 1066, 1049, 1029, 995, 979, 951, 928, 905, 840, 766, 709 $cm^{-1}$.

EXAMPLE 38

Isonicotinoylhydrazone 2-Naphthaldehyde

This compound was prepared in 94% yield from the reaction of isonicotinic acid hydrazide and 2-naphthaldehyde, mp 176–177° C. (uncorr), IR ν 3185, 1669, 1652, 1568, 1558, 1419, 1335, 1293, 1180, 1141, 1075, 1064, 998, 934, 955, 922, 896, 883, 863, 847, 835, 753, 740, 721 $cm^{-1}$.

Example 39

Isonicotinoylhydrazone 2-Methoxy-1-Naphthaldehyde

This compound was prepared in 71% yield from the reaction of isonicotinic acid hydrazide and 2-methoxy-1-naphthaldehyde, mp 202–203° C. (uncorr), IR ν 3181, 1646, 1623, 1584, 1546, 1508, 1404, 1339, 1289, 1272, 1250, 1184, 1150, 1084, 1067, 1041, 1023, 991, 961, 934, 908, 862, 838, 807, 778, 752, 744, 705 $cm^{-1}$.

Example 40

Isonicotinoylhydrazone 1-Naphthaldehyde

This compound was prepared in 83% yield from the reaction of isonicotinic acid hydrazide and l-naphthaldehyde, mp 208–209° C. (uncorr), IR ν 3174, 1676, 1599, 1573, 1541, 1507, 1408, 1338, 1281, 1211, 1176, 1146, 1089, 1074, 1059, 1016, 996, 942, 914, 848, 804, 777, 744, 703 $cm^{-1}$.

Example 41

Isonicotinoylhydrazone of 2-Chlorobenzaldehyde. This compound was prepared using the General Structural Outline for Schiff Base Synthesis. 66% yield of the isonicotinoylhydrazone of 2-chlorobenzaldehyde, mp 218–221° C.; IR ν 3150, 1673, 1600, 1552, 1517, 1494, 1412, 1341, 1322, 1282, 1217, 1157, 1131, 1068, 1047, 1027, 1002, 958, 926, 876, 842, 765, 732, 713 $cm^{-1}$; NMR (300 Mhz) δ 12.3 (1H, br s), 8.9 (1H, s), 8.8 (2H, d, J=6 cps), 8.1 (1H, m), 7.9 (2H, d, J=6 cps), 7.4–7.6 (3H, m) was obtained.

Analysis. Calculated for $C_{13}H_{10}N_3OCl$: C, 60.13; H, 3.88. Found: C, 60.11; H, 3.86.

Example 42

Isonicotinoylhydrazone of 4-Bromobenzaldehyde. With 4-bromobenzaldehyde, one obtained a 91% yield of the isonicotinoylhydrazone of 4-bromobenzaldehyde, mp 218–219° C.; IR ν 3253, 3080, 1657, 1604, 1589, 1552, 1402, 1290, 1217, 1152, 1108, 1067, 1006, 962, 924, 852, 841, 822, 750, 711 $cm^{-1}$; NMR (300 Mhz) δ 12.2 (1H, br s), 8.8 (2H, d, J=6 cps), 8.4 (1H, s), 7.8 (2H, d, J=6 cps), 7.7–7.6 (4H, aromatic pseudo-quartet).

Analysis. Calculated for $C_{13}H_{10}N_3OBr$: C, 51.34; H, 3.31. Found: C, 51.32; H, 3.30.

Example 43

Isonicotinoylhydrazone of 3-Nitrobenzaldehyde

With 3-nitrobenzaldehyde, one obtained an 85% yield of the isonicotinoylhydrazone of 3-nitrobenzaldehyde, mp 225° C. (uncorr); IR ν 3232, 1691, 1609, 1600, 1548, 1524, 1412, 1352, 1314, 1271, 1141, 1101, 1062, 996, 961, 948, 887, 843, 827, 815, 750, 739, 710 $cm^{-1}$.

Analysis. Calculated for $C_{13}H_{10}N_4O_3$: C, 57.78; H, 3.73. Found: C, 57.69; H, 3.77.

Example 44

Isonicotinoylhydrazone of 4-Hexyloxybenzaldehyde

With 4-hexyloxybenzaldehyde, an 87% yield of the isonicotinoylhydrazone of 4-hexyloxybenzaldehyde, mp 135–138° C.; IR ν 3234, 3062, 1650, 1608, 1572, 1549, 1513, 1415, 1398, 1297, 1240, 1179, 1154, 1127, 1112, 1070, 1032, 993, 976, 961, 941, 922, 863, 846, 832, 810, 752, 725 $cm^{-1}$ was obtained.

Analysis. Calculated for $C_{19}H_{23}N_3O_2$: C, 70.06; H, 7.07. Found: C, 70.07; H, 7.07.

Example 45

Isonicotinoylhydrazone of 2-Chloro-5-nitrobenzaldehyde

With 2-chloro-5-nitrobenzaldehyde, the General Structural Outline for Schiff Base Synthesis was used to get a quantitative yield of the isonicotinoylhydrazone of 2-chloro-5-nitrobenzaldehyde, mp 239° C. (uncorr); IR ν 3356, 3102, 1690, 1608, 1574, 1536, 1395, 1352, 1303, 1248, 1186, 1094, 1058, 1003, 938, 916, 846, 818, 738, 637 $cm^{-1}$.

Analysis. Calculated for $C_{13}H_9N_4O_3C_1 \times 0.5H_2O$: C, 49.77; H, 3.21. Found: C, 50.02; H, 3.09.

Example 46

Isonicotinoylhydrazone of 4-Chloro-3-nitrobenzaldehyde

With 4-chloro-3-nitrobenzaldehyde, the General Structural Outline for Schiff Base Synthesis to get a quantitative yield of the isonicotinoylhydrazone of 4-chloro-3-nitrobenzaldehyde, mp 23° C. (uncorr); IR ν 3189, 1685, 1599, 1558, 1530, 1412, 1351, 1277, 1252, 1214, 1154, 1125, 1074, 1061, 1049, 998, 962, 942, 896, 846, 823, 748, 721 $cm^{-1}$ was used.

Analysis. Calculated for $C_{13}H_9N_4O_3Cl$: C, 51.25; H, 2.98. Found: C, 51.20; H, 2.90.

Example 47

Isonicotinoylhydrazone of 2-Nitrobenzaldehyde

With 2-nitrobenzaldehyde, a 97% yield of the isonicotinoylhydrazone of 2-nitrobenzaldehyde, mp 230° C. (uncorr); IR ν 3188, 1678, 1602, 1556, 1515, 1413, 1315, 1287, 1273, 1214, 1149, 1139, 1062, 998, 964, 932, 920, 880, 856, 848, 836, 788, 744 $cm^{-1}$ was obtained.

Analysis. Calculated for $C_{13}H_{10}N_4O_3$: C, 57.78; H, 3.73. Found: C, 57.51; H, 3.65.

Example 48

Isonicotinoylhydrazone of 2.6-Dichlorobenzaldehyde.

With 2,6-dichlorobenzaldehyde, 97% yield of the isonicotinoylhydrazone of 2,6-dichlorobenzaldehyde as an oily solid; IR ν 3150, 1681, 1605, 1592, 1555, 1416, 1354, 1274, 1222, 1192, 1148, 1000, 925, 842, 791, 778, 752, 720 $cm^{-1}$ was obtained.

Analysis. Calculated for $C_{13}H_9N_3OCl_2$: C, 53.08; H, 3.08. Found: C, 53.28; H, 3.21.

Example 49

Isonicotinoylhydrazone of 2,3-Dichlorobenzaldehyde.

With 2,3-dichlorobenzaldehyde, a 98% yield of the isonicotinoylhydrazone of 2,3-dichlorobenzaldehyde, mp 227° C. (uncorr); IR ν 3188, 1687, 1602, 1585, 1547, 1497, 1411, 1350, 1278, 1248, 1214, 1189, 1155, 1141, 1096, 1060, 1042, 997, 972, 940, 848, 783, 742, 708 $cm^{-1}$ was obtained.

Analysis. Calculated for $C_{13}H_9N_3OCl_2$: C, 53.08; H, 3.08. Found: C, 53.16; H, 3.20.

Example 50

Isonicotinoylhydrazone of Acetophenone

With acetophenone, 92% yield of the isonicotinoylhydrazone of acetophenone mp 169–170° C.; IR ν 3173, 1652, 1599, 1540, 1288, 1150, 1103, 975, 835, 757, 722 $cm^1$ was obtained.

Analysis. Calculated for $C_{14}H_{13}N_3O$: C, 70.27; H, 5.48. Found: C, 70.18; H, 5.51.

Example 51

Isonicotinoylhydrazone of 3,4-Difluorobenzaldehyde

This compound was prepared using the General Structural Outline for Schiff Base Synthesis. 86% yield of the isonicotinoylhydrazone of 3,4-difluorobenzaldehyde, mp 195–196° C.; IR ν 3167, 1677, 1624, 1598, 1552, 1523, 1507, 1341, 1301, 1265, 1150, 1109, 960, 942, 866, 817, 777, 753, 721, 712 $cm^1$; NMR (300 Mhz) δ12.2 (1H, s, vanished upon addition of –4 $D_2O$), 8.8 (2H, d, J=6 cps), 8.5 (1H, s), 7.8–7.4 (5H, m, including emergent 7.8 d, J=6 cps) was obtained.

Analysis. Calculated for $C_{13}H_9N_3OF_2$: C, 59.77; H, 3.47. Found: C, 59.64; H, 3.46.

Example 52

Isonicotinoylhydrazone of 2,6-Difluorobenzaldehyde

This compound was prepared using the General Structural Outline for Schiff Base Synthesis. A quantitative yield of the isonicotinoylhydrazone of 2,6-difluorobenzaldehyde, mp 239° C. (uncorr); IR ν 3161, 1654, 1624, 1608, 1569, 1550, 1412, 1305, 1238, 1154, 1076, 1066, 1000, 960, 926, 840, 782, 758, 728 $cm^{-1}$ was obtained.

Analysis. Calculated for $C_{13}H_9N_3OF_2$: C, 59.77; H, 3.47. Found: C, 59.92; H, 3.70.

Example 53

Isonicotinoylhydrazone of 3.4-Dichlorobenzaldehyde

With 3,4-dichlorobenzaldehyde, an 88% yield of the isonicotinoylhydrazone of 3,4-dichlorobenzaldehyde mp 241–244° C. (uncorr); IR ν 3178, 1682, 1590, 1552, 1413, 1352, 1278, 1215, 1147, 1121, 1078, 1062, 1028, 999, 952, 937, 886, 846, 813, 747, 722 $cm^{-1}$ was obtained.

Analysis. Calculated for $C_{13}H_9N_3OCl_2$: C, 53.08; H, 3.08. Found: C, 52.85; H, 3.20.

Example 54

Isonicotinoylhydrazone of 4-Chlorobenzaldehyde. This compound was prepared using the General Structural Outline for Schiff Base Synthesis. 94% yield of the isonicotinoylhydrazone of 4-chlorobenzaldehyde, mp 215–216° C.; IR ν 3167, 1660, 1611, 1597, 1412, 1219, 1158, 1118, 1087, 1012, 952, 1000, 879, 838, 818, 751, 722 $cm^{-1}$ was obtained.

Analysis. Calculated for $C_{13}H_{10}N_3OCl$: C, 60.13; H, 3.88. Found: C, 60.05; H, 3.89.

Example 55

Isonicotinoylhydrazone of Ethyl 2-Oxo-4-phenylbutyrate

This compound was prepared using the General Structural Outline for Schiff Base Synthesis. 90% yield of the isonicotinoylhydrazone of ethyl 2-oxo-4-phenylbutyrate, mp 104° C.; IR ν 3251, 1702, 1685, 1592, 1554, 1511, 1417, 1403, 1301, 1246, 1213, 1143, 1112, 1074, 1022, 994, 942, 875, 843, 798, 764, 754, 721, 706 $cm^{-1}$ was obtained.

Analysis. Calculated for $C_{18}H_{19}N_3O_3$: C, 66.45; H, 5.89. Found: C, 66.10; H, 5.96.

Example 56

Isonicotinoylhydrazone of beta-Phenylcinnamaldehyde

This compound was prepared using the General Structural Outline for Schiff Base Synthesis. 86% yield of the isonicotinoylhydrazone of beta-phenylcinnamaldehyde, mp 223° C.; IR ν 3187, 1649, 1604, 1564, 1546, 1523, 1403, 1344, 1298, 1284, 1208, 1155, 1133, 1075, 1062, 1016, 992, 935, 916, 891, 880, 842, 771, 758, 745, 720 $cm^{-1}$ was obtained.

Analysis. Calculated for $C_{21}H_{17}N_3O$: C, 77.04; H, 5.23. Found: C, 76.78; H, 5.36.

Example 57

Isonicotinoylhydrazone of Di-2-Pyridyl Ketone

This compound was prepared using the General Structural Outline for Schiff Base Synthesis. 83% yield of the isonicotinoylhydrazone of di-2-pyridyl ketone, mp 150° C.; IR ν 3363, 1699, 1583, 1513, 1432, 1320, 1283, 1263, 1224, 1135, 1112, 1093, 1077, 1054, 994, 970, 946, 905, 897, 842, 806, 789, 742 $cm^{-1}$ was obtained.

Analysis. Calculated for $C_{17}H_{13}N_5O\times2H_2O$: C, 60.17; H, 5.04. Found: C, 60.11; H, 5.04.

Example 59

Isonicotinoylhydrazone of 2.4-Pentanedione.

This compound was prepared using the General Structural Outline for Schiff Base Synthesis. 85% yield of the monoisonicotinoylhydrazone of 2,4-pentanedione, mp 136° C., lit mp 131–133° C. [Yale et al., *Journal of Organic Chemistry,* 75, 1933 (1953)]; IR ν 3150, 1622, 1597, 1545, 1329, 1245, 1229, 1205, 1141, 1112, 1065, 1021, 1003, 971, 870, 840, 755, 736, 703 $cm^{-1}$ was obtained.

General Structural Outline for Diacylhydrazine Synthesis

A. Acylation Procedure.

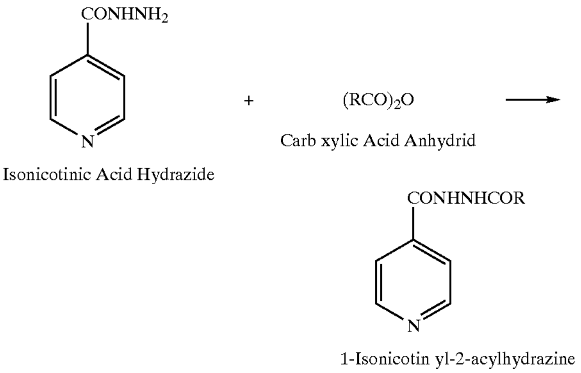
Isonicotinic Acid Hydrazide
Carb xylic Acid Anhydrid
1-Isonicotin yl-2-acylhydrazine Diacylhydrazine compounds are prepared by the reaction of isonicotinic acid hydrazide with carboxylic acid anhydrides. Reaction conditions and work-up methods are critical to insure that the products of the syntheses are obtained in acceptable form. Further, solvent choice and reaction times are critical to insure formation of the diacylhydrazine, preventing over-acylation.

Isonicotinic acid hydrazide (Fluka A.-G., Lancaster or Aldrich Chemical Companies) is weighed into a round bottom flask fitted for reflux with a temperature-controlled heating mantle, reflux condenser and magnetic stirrer. The volume of the flask is chosen in such a way that the contents of the entire reaction mixture do not exceed 50% of the flask's nominal capacity.

Sufficient diethyl ether (EM Science absolute grade) is added to make the ratio of isonicotinic acid hydrazide to ether to be about 0.10 to 1.00. This solvent choice is necessary to insure that the desired diacylhydrazine product is formed and not the triacylhydrazine product of over-acylation.

The mixture is brought to the boil and remains a heterogeneous mixture throughout the entire procedure. A 1.33 Molar solution of the appropriate carboxylic acid anhydride in ether is added through the top of the condenser in several small portions over a period not to exceed 0.004 moles per minute.

After the addition is complete, the mixture is stirred and refluxed for an additional 20 minutes. The mixture is allowed to cool to room temperature and to stand over night. A white solid forms and this is the desired product.

The white solid product thus obtained is filtered off by gravity using Whatman No. 1 filter paper, washed with cold ether (4 mL per 0.010 mole of product, assuming complete conversion) and allowed to air dry. The product is then analyzed and characterized by the usual means, including melting point, infrared, near infrared, mass and magnetic resonance spectroscopy and elemental analysis.

Experimental Procedures-Diacylhydrazines

Example 1

1-Isonicotinoyl-2-formylhydrazine

This reaction was performed to produce 1-isonicotinoyl-2-formylhydrazine by mixing formic acid (88% by weight, 2 mL) with isonicotinic acid hydrazide (1.03 g) and allowing the mixture to stir at room temperature. An exotherm was noted, heat was produced, and after several minutes a clear fluorescent yellow solution was obtained. The yellow solution was permitted to stand over night, poured into ether (20 mL), yielding a white crystalline solid. The solid was stirred and crushed with ether (20 mL) and allowed to air dry for several hours, giving the diacylhydrazine 1,1-isonicotinoyl-2-formylhydrazine (1.12 g, 90%) mp 94–96° C., lit mp [H. Fox, U.S. Pat. No. 2,689,852; Sep. 21, 1954; *Chem. Abstr.,* 1955, 49, 14813d] 96–98° C.; IR ν 3252, 1695, 1662, 1611, 1556, 1415, 1333, 1246, 1227, 1069, 1021, 850 $cm^{-1}$.

Example 2

1-Isonicotinoyl-2-acetylhydrazine

1-Isonicotinoyl-2-acetylhydrazine was prepared using the Acylation Method in the General Structural Outline for Diacylhydrazine Synthesis in a like manner in 96% yield, mp 158–160° C. (from butyl acetate), lit mp [A. Novotny, Z. Brezik, J. Pridal and K. Kalfurs, *Ceskoslov. farm.,* 1958, 7, 517–520; *Chem. Abstr.,* 1959, 53, 10191c] 162.2–162.5° C.; IR ν 3214, 1699, 1657, 1555, 1514, 1296, 1222, 997, 838, 755 $cm^{-1}$.

Example 3

1-Isonicotinoyl-2-propionylohydrazine

1-Isonicotinoyl-2-propionylhydrazine was prepared using the Acylation Method in the General Structural Outline for Diacylhydrazine Synthesis in a like manner in 95% yield, mp 131° C., lit mp [A. Novotny, Z. Brezik, J. Pridal and K. Kalfurs, *Ceskoslov. farm.,* 1958, 7, 517–520; *Chem. Abstr.,* 1959, 53, 10191c] 130° C.; IR ν 3195, 1671, 1599, 1551, 1494, 1403, 1218, 1060, 859, 845 $cm^{-1}$.

Example 4

1-Isonicotinoyl-2-butyrylhydrazine

1-Isonicotinoyl-2-butyrylhydrazine was prepared using the Acylation Method in the General Structural Outline for Diacylhydrazine Synthesis in a like manner in 87% yield, mp 142° C., lit mp [A. Novotny, Z. Brezik, J. Pridal and K. Kalfurs, *Ceskoslov. farm.,* 1958, 7, 517–520; *Chem. Abstr.,* 1959, 53, 10191c] 140° C.; IR ν 3195, 1598, 1552, 1495, 1402, 1217, 1085, 881, 845 $cm^{-1}$.

Example 5

1-Isonicotinoyl-2-valeroylhydrazine

1-Isonicotinoyl-2-valeroylhydrazine was formed in the following way. This compound was prepared using the Acylation Method in the General Structural Outline for Diacylhydrazine Synthesis. To a heterogeneous mixture of isonicotinic acid hydrazide (1.38 g, 10.1 mmol) in a) boiling ether (15 mL) contained in a 100 mL round bottom flask fitted for reflux with a temperature-controlled heating mantle and reflux condenser and for magnetic stirring was added in several small portions over 5 minutes valeric anhydride (4.1 mL, D=0.92 g/mL, 3.77 g, 20.3 mmol) dissolved in ether (15 mL). After the addition was complete, the mixture was stirred and refluxed a further 20 minutes, then allowed to cool to room temperature and stand over night. The white micaceous crystalline solid thus obtained was filtered off by gravity and washed liberally with ether (40 mL) to give the 1-isonicotinoyl-2-valeroylhydrazine compound (1.73 g, 78%), mp 162° C. (from butyl acetate); IR ν 3192, 1599, 1551, 1493, 1400, 1119, 1085, 1062, 869, 846, 756 $cm^{-1}$.

Analysis. Calculated for $C_{11}H_{15}N_3O_2$: C, 59.71; H, 6.83. Found: C, 59.86; H, 6.75.

B. Thioacylation Procedure.

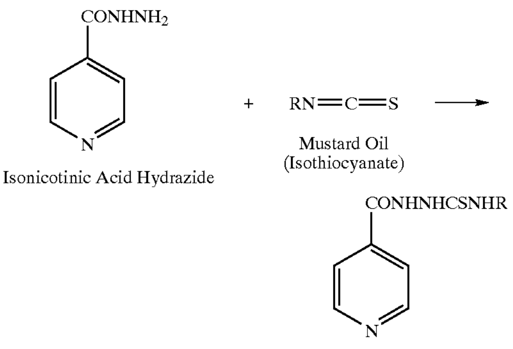

Isonicotinic Acid Hydrazide

Mustard Oil (Isothiocyanate)

1-Arylthioamido-2-Isonicotinoylhydrazine

The thioacylated compounds are prepared by the reactions of isonicotinic acid hydrazide LD with mustard oils (isothiocyanates).

Isonicotinic acid hydrazide (Fluka A.-G., Lancaster or Aldrich Chemical Companies) is used to prepare a 0.4 Molar solution in absolute ethanol, at reflux. The ethanol is used as a received from Pharmco, Incorporated.

The preparation of the solution at reflux is done by mixing the required weight of isonicotinic acid hydrazide with the necessary volume of absolute ethanol in a standard taper round bottom flask fitted for reflux with a temperature-controlled heating mantle, carborundum boiling chip and condenser. The volume of the flask is chosen in such a way that the contents of the entire reaction mixture do not exceed 50% of the flask's nominal capacity.

The mixture of isonicotinic acid hydrazide and ethanol is brought to the boil and forms a clear colorless solution. The appearance of pronounced yellow color or pink tinge in the boiling mixture is unacceptable and generally indicates impure isonicotinic acid hydrazide.

To the clear colorless solution at the boil is added through the condenser the appropriate mustard oil (isothiocyanate) as a 0.60 Molar solution in ethanol at a rate no greater than 0.0006 moles per minute. Refluxing is continued for one hour, at which point the solution is usually yellow to orange, depending on the individual nature of the mustard oil.

The reaction mixture is allowed to cool to room temperature and to stand over night, depositing white crystals of product. The material is filtered off by gravity filtration using Whatman No. 1 filter paper and allowed to stand on the filter cake to dry for several hours, yielding the thioacylated product, generally in analytically pure form. The arylthioamido product is then analyzed and characterized by the usual means, including melting point, infrared, mass and magnetic resonance spectroscopy and elemental analysis.

EXAMPLES

Example 1

Phenylthioamido-2-isonicotinoylhydrazine

This compound was prepared using the Thioacylation Method in the General Structural Outline for Diacylhydrazine Synthesis. To a clear colorless solution of isonicotinic acid hydrazide (0.82 g, 6.0 mmol) in boiling ethanol (50 mL), in a 100 mL round bottom flask fitted for reflux, was added 0.81 g (6.0 mmol) of phenylisothiocyanate dissolved in ethanol (10 mL) in several small portions over a period of 10 minutes. Refluxing was continued for one hour, at which point the solution was orange. The reaction mixture was permitted to stand at room temperature over night, depositing white crystals of product. The material was filtered off by gravity and allowed to stand on the filter cake to dry for several hours, yielding 1.18 g (72%) of the title compound, mp 176–177° C., IR ν 3300-3150, 1682, 1666, 1598, 1498, 1404, 1303, 1255, 1215, 1142, 1101, 1065, 1030, 1001, 964, 944, 902, 843, 754, 741, 690 $cm^{1}$.

Analysis. Calculated for $C_{13}H_{12}N_4SO$: C, 57.34; H, 4.44. Found: C, 57.41; H, 4.43.

Example 2

1-para-Tolylthioamido-2-isonicotinoylhydrazine

This compound was prepared using the Thioacylation Method in the General Structural Outline for Diacylhydrazine Synthesis. To a clear colorless solution of isonicotinic acid hydrazide (0.82 g, 6.0 mmol) in boiling ethanol (50 mL), in a 100 mL round bottom flask fitted for reflux, was added 0.89 g (6.0 mmol) of para-tolylisothiocyanate dissolved in ethanol (10 mL) in several small portions over a period of 10 minutes. Refluxing was continued for one hour, at which point the solution was yellow-orange. The reaction mixture was permitted to stand at room temperature over night, depositing white crystals of product. The material was filtered off by gravity and allowed to stand on the filter cake to dry for several hours, yielding 1.46 g (91%) of the title compound, mp 182–184° C., IR ν 3300-3150, 1681, 1667, 1600, 1552, 1512, 1305, 1255, 1211, 1140, 1065, 1020, 996, 965, 940, 905, 844, 816, 753, 720 $cm^{-1}$.

Analysis. Calculated for $C_{14}H_{14}N_4SO$: C, 58.72; H, 4.93. Found: C, 58.81; H, 4.93.

Example 3

1-para-Bromophenylthioamido-2-isonicotinoylhydrazine

This compound was prepared using the Thioacylation Method in the General Structural Outline for Diacylhydrazine Synthesis from isonicotinic acid hydrazide and para-bromophenylisothiocyanate in 76% yield, mp 178–180° C., IR ν 3300-3150, 1672, 1600, 1548, 1299, 1254, 1212, 1145, 1065, 1011, 1000, 936, 900, 824, 750, 722 $cm^{1}$.

Analysis. Calculated for $C_{13}H_{11}N_4SOBr$: C, 44.46; H, 3.16. Found: C, 44.42; H, 3.26.

Example 4

1-para-Chlorophenylthioamido-2-isonicotinoylhydrazine

This compound was prepared using the Thioacylation Method in the General Structural Outline for Diacylhydrazine Synthesis from isonicotinic acid hydrazide and para-chlorophenylisothiocyanate in 77% yield, mp 181–182° C., IR ν 3300-3150, 1674, 1650, 1596, 1550, 1512, 1404, 1300, 1256, 1213, 1148, 1090, 1064, 1044, 1000, 965, 937, 902, 828, 752, 717 $cm^{-1}$.

Analysis. Calculated for $C_{13}H_{11}N_4SOCl$: C, 50.90; H, 3.61. Found: C, 50.91; H, 3.70.

General Structural Outline for Oxadiazoline Synthesis

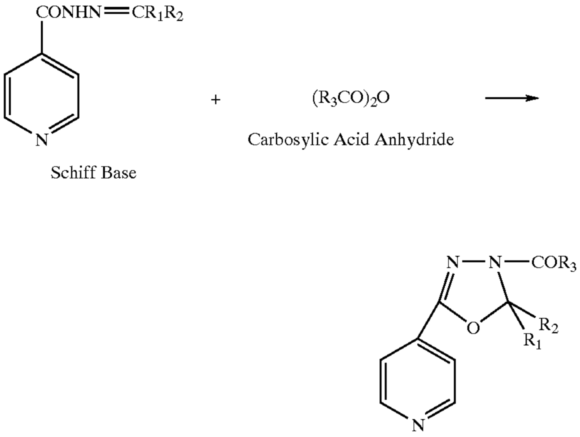

Schiff Base

Carbosylic Acid Anhydride

Oxadiazoline

Oxadiazolines are prepared by the reactions of Schiff bases with carboxylic acid anhydrides. Reaction conditions, specifically including reaction times, and work-up methods, specifically including a base wash, are critical to insure that the products of the syntheses are obtained in acceptable form.

The appropriate Schiff base is weighed into a pear-shaped standard taper flask. The volume of the flask is chosen in such a way that the contents of the entire reaction mixture do not exceed 50% of the flask's nominal capacity. A boiling chip is added to the flask, and the flask is fitted for reflux with a temperature-controlled heating mantle and reflux condenser.

Sufficient carboxylic acid anhydride (typically acetic anhydride) is added to the flask to make the solution about a 0.25–0.30 Molar solution of Schiff base in anhydride. This characteristically makes the mole ratio of Schiff base to anhydride to be about 0.028 to 1.00. The mixture is brought to the boiling point, and refluxing is continued for an hour. During the hour of refluxing, the reaction mixture changed color and may vary in color from light yellow to deep orange.

Following the hour of refluxing, the hot mixture is turned out onto a large watchglass and allowed to air dry in the hood over night. The solid tan-colored material thus obtained shows the expected infrared bands for the oxadiazoline, viz., infrared bands at ca. 1670, 1630, 1600, 1550 and 1520, diagnostic for the completion of the desired reaction.

The material is taken up in sufficient ether (EM Science absolute grade) to make a 0.04 to 0.05 Molar solution of product oxadiazoline in ether, assuming complete conversion of Schiff base to oxadiazoline, i.e. the material is taken up in an amount of ether six times the volume of anhydride used for the reaction.

In a large beaker with at least twice the nominal capacity of the mixture it will contain, fitted with a magnetic stirrer, the ether solution is stirred vigorously over 10% aqueous sodium bicarbonate solution for 90 minutes. This base wash is necessary to insure that the final product is obtained in pure form.

The mixture is transferred to a separatory funnel, and the ether layer is separated. The volume of the ether layer is noted. The aqueous layer is then extracted with three portions of ether, each of which is one-half the volume so noted.

The combined ether extracts are dried over anhydrous magnesium sulfate (Baker) for several hours, gravity filtered through Whatman No. 1 filter paper and evaporated on a large watchglass to give the oxadiazoline. The beige to tan solid product thus obtained is then analyzed and characterized by the usual means, including melting point, infrared, mass and magnetic resonance spectroscopy and elemental analysis.

EXPERIMENTAL PROCEDURES-OXADIAZOLINES

Example 1

2.2-Dimethyl-3-propionyl-5-(4-pyridyl)-1,3,4-oxadiazoline

The title compound was prepared by the General Structural Outline for Oxadiazoline Synthesis from the isonicotinoylhydrazone of acetone and propionic anhydride. Thus to the isonicotinoylhydrazone of acetone (0.355 g, 2.01 mmol) in a standard 50 mL pear-shaped flask containing a boiling chip and fitted for reflux with a temperature-controlled heating mantle and reflux condenser was added propionic anhydride (10 mL, an excess). The mixture was brought to the boiling point, and refluxing was continued for an hour. After 45 minutes of reflux, the sample had become a deep orange color. Following the hour of refluxing, the hot mixture was turned out onto a watchglass and allowed to air dry in the hood over night. The material thus obtained (100% of theory) showed the expected infrared bands for the oxadiazoline, and only a small amount of the anhydride remained. The material was taken up in ether (30 mL), and the ether solution was stirred vigorously over 10% aqueous sodium bicarbonate solution for 90 minutes, during which time a substantial amount of the color passed into the aqueous layer. The ether was drawn off, and the aqueous portion was extracted with 3×15 mL portions of ether. The combined ether layers were dried over anhydrous magnesium sulfate, filtered and evaporated on a watchglass in the hood to give the product oxadiazoline (0.397 g, 85%) as a tan semisolid mass; IR ν 3030, 1676, 1625, 1597, 1551, 1498, 1093, 840, 826 $cm^{-1}$.

Analysis. Calculated for $C_{12}H_{15}N_3O_2$: C, 61.79; H, 6.48. Found: C, 62.16; H, 6.67.

Example 2

2,2-Dimethyl-3-acetyl-5-(4-pyridyl)-1,3,4-oxadiazoline

The title compound was prepared by the General Structural Outline for Oxadiazoline Synthesis from the isonicotinoylhydrazone of acetone and acetic anhydride in 99% yield as hexagonal plates, mp 117–118° C., lit mp [H. Yale, K. Losee, J. Martins, M. Holsing, F. Perry and J. Bernstein, *J. Am. Chem. Soc.,* 75, 1933 (1953)] 109–111° C.; IR ν 3032, 1665, 1625, 1598, 1550, 1505, 1085, 1047, 1039, 968, 945, 839, 826, 735 $cm^{-1}$.

Example 3

2.2-Pentamethylene-3-acetyl-5-(4-pyridyl)-1,3,4-oxadiazoline

The title compound was prepared from the isonicotinoylhydrazone of cyclohexanone and acetic anhydride. Specifically, to the isonicotinoylhydrazone of cyclohexanone (0.502 g, 2.31 mmol), dissolved in toluene (10 mL) in a 50 mL pear-shaped flask containing a boiling chip and fitted for reflux with a temperature-controlled heating mantle and reflux condenser was added acetic anhydride (1 mL, 11 mmol), dissolved in toluene (5 mL). The mixture was brought to the boiling point, and there by was produced a clear yellow solution. Refluxing was continued for 8.5 hours. Following the period of refluxing, the hot mixture was turned out onto a watchglass and allowed to air dry in the hood to obtain the product, 0.52 g (87%), mp 106–107° C. (from petroleum ether), lip mp [R. Sagitulin and A. Kost, *Vestnik Moskov. Univ., Ser. Mat., Mekh., Astron., Fiz. i Khim.,* 14, 187 (1959); *Chem. Abstr.,* 54, 17383h (1959)] 104–105° C.; IR ν 3030, 1678, 1628, 1598, 1552, 1504, 892, 846, 827, 734, 6650□$cm^1$.

Example 4

2-(2,6-Dichlorophenyl)-3-acetyl-5-(4-pyridyl)-1,3,4-oxadiazoline

The title compound was prepared from the isonicotinoylhydrazone of 2,6-dichlorobenzaldehyde and acetic anhydride, using the General Structural Outline for Oxadiazoline Synthesis in 35% yield, mp 163° C.; NMR (300 Mhz) δ □8.77 (2H, d, J=6 cps), 7.7–7.5 (6H, m including emergent d at 7.6, J=6 cps), 2.2 (3H, s).

Analysis. Calculated for $C_{15}H_{11}N_3O_2Cl_2$: C, 53.59; H, 3.30. Found: C, 53.58; H, 3.37.

Example 5

2-Methyl-2-phenyl-3-acetyl-5-(4-pyridyl)-1,3,4-oxadiazoline

The title compound was prepared from the isonicotinoylhydrazone of acetophenone and acetic anhydride, using the General Structural Outline for Oxadiazoline Synthesis in 75% yield, mp 79–81° C.; IR ν □1667, 1628, 1597, 1551, 1329, 1311, 1258, 1216, 1199, 1157, 1084, 1062, 1028, 989, 956, 892, 830, 767, 722□$cm^{-1}$; $^1$H NMR (300 Mhz) δ □8.7

(2H, d, J=6 cps), 7.7 (2H, d, J=6 cps), 7.5–7.3 (5H, m), 2.3 (3H, s), 2.2 (3H, s); $^{13}C$ NMR δ 166, 153, 151, 138, 132, 129, 127, 125, 121, 102, 22.5, 22.7.

Example 6

2-(2,6-Difluorophenyl)-3-acetyl-5-(4-pyridyl)-1,3,4-oxadiazoline

The title compound was prepared from the isonicotinoylhydrazone of 2,6-difluorobenzaldehyde and acetic anhydride, using the General Structural Outline for Oxadiazoline Synthesis in 31% yield, mp 119–121° C.; IR ν 1673, 1624, 1594, 1554, 1334, 1312, 1295, 1209, 1092, 1062, 1008, 988, 974, 886, 825, 790, 730, 703, 663, 632 $cm^{-1}$; NMR (300 Mhz) δ 8.75 (2H, □□br d, J=6 cps), 7.75 (2H, d, J=6 cps), 7.65–7.15 (4H, m from which emerges singlet at 7.5), 2.2 (3H, s).

Analysis. Calculated for $C_{15}H_1N_3O_2F_2$: C, 59.41; H, 3.66. Found: C, 59.17; H, 3.70.

Example 7

2-(4-Chloro-3-nitrophenyl)-3-acetyl-5-(4-pyridyl)-1,3,4-oxadiazoline

The title compound was prepared from the isonicotinoylhydrazone of 4-chloro-3-nitrobenzaldehyde and acetic anhydride, using the General Structural Outline for Oxadiazoline Synthesis in 50% yield, mp 122° C.; IR ν 1663, 1626, 1597, 1574, 1554, 1532, 1310, 1264, 1212, 1167, 1135, 1089, 1052, 1009, 974, 924, 914, 869, 840, 831, 815, 754, 730, 700 $cm^{-1}$.

Analysis. Calculated for $C_{15}H_{11}N_4O_4Cl$: C, 51.96; H, 3.20. Found: C, 51.75; H, 3.33.

Example 8

2-(2-Nitrophenyly)-3-acetyl-5-(4-pyridyl)-1,3,4-oxadiazoline

The title compound was prepared from the isonicotinoylhydrazone of 2-nitrobenzaldehyde and acetic anhydride, using the General Structural Outline for Oxadiazoline Synthesis in 91% yield, mp 159° C.; IR ν 1663, 1628, 1598, 1581, 1551, 1522, 1414, 1333, 1314, 1270, 1205, 1172, 1146, 1088, 1082, 1032, 988, 896, 851, 828, 798, 750, 714, 705 $cm^{-1}$.

Analysis. Calculated for $C_{15}H_{12}N_4O_4$: C, 57.70; H, 3.87. Found: C, 57.65; H, 3.98.

Example 9

2-(3,4-Difluorophepyl)-3-acetyl-5-(4-pyridyl)-1,3,4-oxadiazoline

To the isonicotinoylhydrazone of 3,4-difluorobenzaldehyde (0.38 g, 1.4 mmol) in a 50 nm pear-shaped flask containing a boiling chip and fitted for reflux with a temperature-controlled heating mantle and reflux condenser was added acetic anhydride (5 mL, 49 mmol, an excess). The mixture was brought to the boiling point, and refluxing was continued for an hour. Following the hour of refluxing, the hot mixture was turned out onto a watchglass and allowed to air dry in the hood over night. The material obtained showed the expected infrared bands for the title oxadiazoline, and only a small amount of the anhydride remained. The material was taken up in ether (30 mL), and the ether solution was stirred vigorously over 10% aqueous sodium bicarbonate solution for 90 minutes. The ether was drawn off, and the aqueous portion was extracted with 3×15 mL portions of ether. The combined ether layers were dried over anhydrous magnesium sulfate, filtered and evaporated on a watchglass in the hood to give the title oxadiazoline (0.44 g, 100%) as a slightly hygroscopic beige solid, mp 112–113° C.; IR ν 1667, 1629, 1600, 1552, 1519, 1413, 1339, 1321, 1281, 1217, 1184, 1116, 1092, 1076, 1066, 1043, 990, 969, 954, 925, 872, 828, 818, 794, 770, 751, 704 $cm^{-1}$; NMR (300 Mhz) δ 8.75 (2H, d, J=6 cps), 7.75–7.38 (5H, m, including emergent 7.75 d, J=6 cps), 7.23 (1H, s), 2.2 (3H, s); high resolution mass spectrum (FAB method) m/z 304.0889 (M+H) ($C_{15}H_{11}N_3O_2F_2$+H requires 304.0898).

Analysis. Calculated for $C_{15}H_{11}N_3O_2F_2 \times 0.25H_2O$: C, 58.53; H, 3.76. Found: C, 58.78; H, 3.67.

Example 10

2-(3.4-Dichlorophenyl)-3-acetyl-5-(4-pyridyl)-1,3,4-oxadiazoline

The title compound was prepared from the isonicotinoylhydrazone of 3,4-dichlorobenzaldehyde and acetic anhydride, using the General Structural Outline for Oxadiazoline Synthesis in 36% yield, mp 101–104° C., IR ν 1667, 1628, 1598, 1552, 1410, 1365, 1334, 1314, 1266, 1212, 1169, 1130, 1094, 1072, 1032, 990, 926, 885, 857, 825, 745, 723, 702 $cm^{-1}$.

Analysis. Calculated for $C_{15}H_{11}N_3O_2Cl_2$: C, 53.59; H, 3.30. Found: C, 53.24; H, 3.45.

Results

In vitro Testing against *M. tuberculosis* and Nontuberculous *Mycobacteria* (NTB)

The compounds of the invention have been initially evaluated by the Tuberculosis Antimicrobial Acquisition and Coordinating Facility (TAACF), and all show significant activity in the Primary Assay.

Summary of TAACF Methods

Primary screening is conducted at 12.5 or 6.25 ug/ml (or molar equivalent of highest molecular weight compound in a series of congeners) against *Mycobacterium tuberculosis* $H_{37}Rv$ (ATCC 27294) in BACTEC 12B medium using the Microplate Alamar Blue Assay (MABA). Compounds exhibiting fluorescence are tested in the BACTEC 460-radiometric system. Compounds effecting <90% inhibition in the primary screen (MIC>6.25 ug/ml) are not generally evaluated further. Compounds demonstrating at least 90% inhibition in the primary screen are re-tested at lower concentrations against *M. tuberculosis* H37Rv to determine the actual minimum inhibitory concentration (MIC) in the MABA. The MIC is defined as the lowest concentration effecting a reduction in fluorescence of 90% relative to controls. Concurrent with the determination of MICs, compounds ar tested for cytotoxicity (IC50) in VERO cells at concentrations less than or equal to 62.5 ug/ml or 10 times the MIC for *M. tuberculosis* H37Rv. After 72 hours exposure, viability is assessed on the basis of cellular conversion of MTT into a formazan product using the Promega CellTiter 96 Non-radioactive Cell Proliferation Assay. Compounds for which the IC50:MIC (SI) ratio is >10 will have in vitro activity confirmed in the BACTEC 460 at 6.25 ug/ml. Compounds are then tested for killing of *M. tuberculosis* Erdman (ATCC 35801) in monolayers of mouse bone marrow macrophages. (EC99 and EC90; lowest concentration effecting a 90% and 99% reduction in colony forming units at 7 days compared to drug-free controls) at 4-fold concentrations equivalent to 0.25, 1, 4 and 16 times the MIC. Concurrent with the testing of compounds in macrophages, MICs are determined in the MABA for three strains of drug-resistant *M. tuberculosis*, (each strain resistant to a single TB drug) as well as *M. avium*. Typically, all compounds progressing to this stage of screening has been tested against *M. avium* (ATCC 25291), *M. tuberculosis* strains resistant to isoniazid (ATCC 35822), rifampin (ATCC 35838), and one other drug resistant strain (the latter determined by the compound type) as well as the drug-sensitive strains H37Rv and Erdman. Minimum bactericidal concentration (MBC) is then determined for *M. tuberculosis* H37Rv and Erdman (and the corresponding drug-resistant strain for analogs of known antitubercular drugs) by subculturing onto drug-free solid following exposure in supplemented Middlebrook 7H9 media to drug concentrations equivalent to and higher than the previously determined MICs of the respective strains.

The EC90 represents bacteriostatic activity, and the EC99 indicates bactericidal activity. The EC90 denotes the effective concentration to give a 90% reduction in intramacrophage bacteria relative to a drug-free control. Since this concentration maintains roughly the level of the initial inoculum, the value represents the necessary amount of drug to maintain a static level of bacteria within the macrophage host. The EC99 value represents a one log reduction and thus gives a measure of the bactericidal activity of the drug. The ratio EC90/MIC provides a measure of bioavailability and metabolism of the active agent within the living host, since it compares the in vitro activity against the *bacillus* to the activity against the *bacillus* while it lives within the host cell. The smaller the EC90(MIC, the better the agent, with the threshold for further screening ~4 (viz., the value for INH itself).

TABLE 1

*M. tuberculosis* Assay

| SAMPLE ID | STRUCTURE | ASSAY | MIC (ug/mg) | SI | MIC H37Rv (ug/ml) | MIC Endman (ug/ml) | MIC INH-R (ug/ml) | INH-R: MIC |
|---|---|---|---|---|---|---|---|---|
| 132358 | 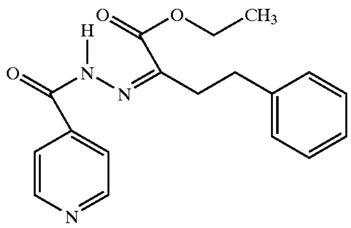 | Bactec | 0.1 | >1250 | 0.1 | 0.1 | >3.2 | >32 |
| 132532 | 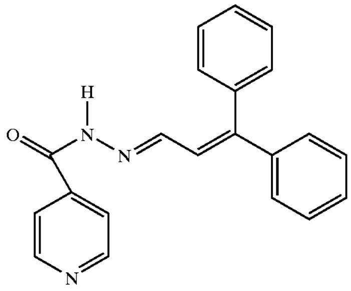 | Bactec | 0.1 | 68 | 0.1 | 0.1 | >3.2 | >32 |

| SAMPLE ID | MIC RMP-R (ug/ml) | RMP-R: MIC | MIC EMB-R (ug/ml) | EMB-R: MIC | MIC ETA-R (ug/ml) | ETA-R: MIC |
|---|---|---|---|---|---|---|
| 132358 | 0.1 | 1 | >3.2 | >32 | 0.8 | 0.08 |
| 132532 | 0.1 | 1 | >3.2 | >32 | 1.6 | 0.16 |

TABLE 2
| *M. avium* Assay | | | |
|---|---|---|---|
| SAMPLE ID | STRUCTURE | ASSAY | MIC (ug/ml) |
| 102044 | 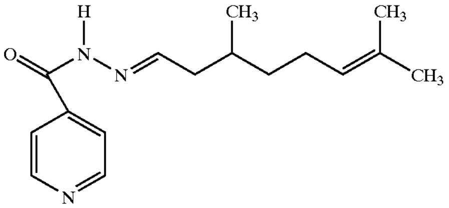 | BACTEC | 0.78 |
| 102866 | 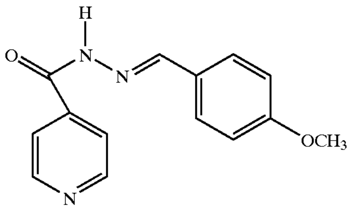 | BACTEC | 3.25 |
| 117150 | 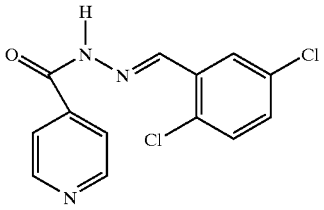 | BACTEC | >3.25 |
TABLE 3
| *M. avium* Assay | | | |
|---|---|---|---|
| SAMPLE ID | STRUCTURE | ASSAY | MIC (ug/ml) |
| 132358 | 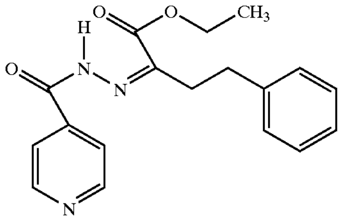 | BACTEC | >3.20 |
TABLE 3-continued
| *M. avium* Assay | | | |
|---|---|---|---|
| SAMPLE ID | STRUCTURE | ASSAY | MIC (ug/ml) |
| 132532 | 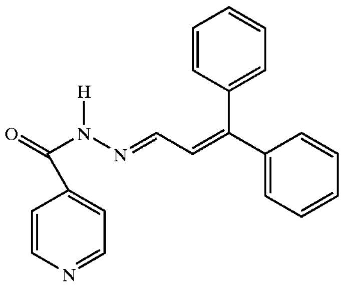 | BACTEC | >3.20 |

TABLE 4
*M. tuberculosis* Assay
| SAMPLE ID | STRUCTURE | MIC (ug/ml) | SI | ASSAY DATE | EC 90 | EC99 | EC 90: MIC | COMMENT |
|---|---|---|---|---|---|---|---|---|
| 102674 | 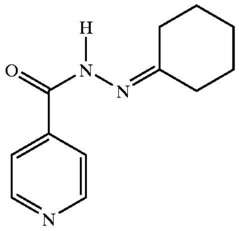 | 0.03 | 40000 | 11/12/98 | 0.08 | >0.4 | 2.67 | EC90 RMP = .1; EC99 RMP = .6 |
| 102752 | 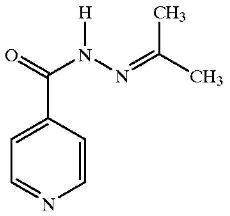 | 0.1 | 10000 | 11/12/98 | 0.03 | 0.14 | 0.3 | EC90 RMP = .06; EC99 RMP = .36 |
| 101743 | 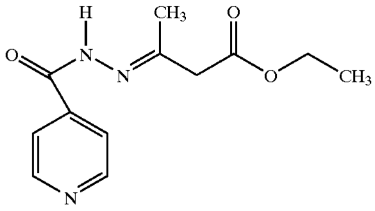 | 0.2 | 50000 | 11/12/98 | 0.01 | >3.2 | 0.05 | EC90 RMP = .1; EC99 RMP = .6 |
| 102858 | 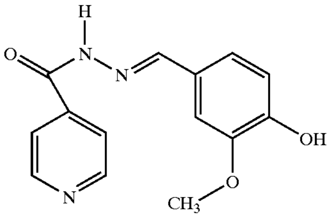 | 0.2 | 4000 | 11/12/98 | 0.03 | 0.12 | 0.15 | EC90 RMP = .02; EC99 RMP = .23 |
| 102090 | 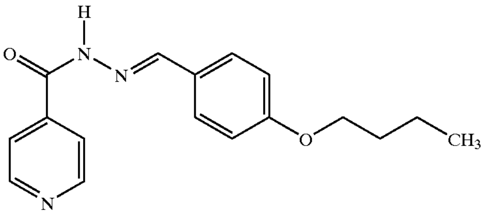 | 0.1 | 2000 | 11/12/98 | 0.18 | >1.6 | 1.8 | EC90 RMP = .1; EC99 RMP = .6 |
| 102787 | 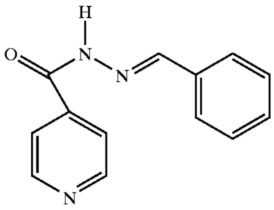 | 0.1 | 2000 | 11/12/98 | 0.04 | 0.12 | 0.4 | EC90 RMP = .02; EC99 RMP = .23 |

TABLE 4-continued
*M. tuberculosis* Assay
| SAMPLE ID | STRUCTURE | MIC (ug/ml) | SI | ASSAY DATE | EC 90 | EC99 | EC 90: MIC | COMMENT |
|---|---|---|---|---|---|---|---|---|
| 102866 | 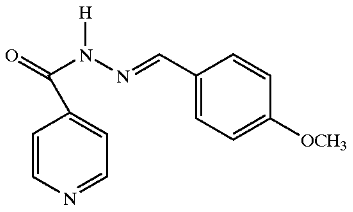 | 0.1 | 1520 | 11/12/98 | 0.04 | 0.15 | 0.4 | EC90 RMP = .02; EC99 RMP = .23 |
| 102044 | 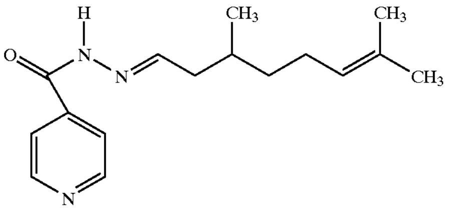 | 0.2 | 1000 | 11/12/98 | 0.02 | 0.08 | 0.1 | EC90 RMP = .02; EC99 RMP = .23 |
| 103167 | 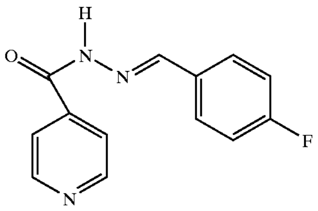 | 0.1 | 1000 | 11/12/98 | 0.02 | 0.07 | 0.2 | EC90 RMP = .02; EC99 RMP = .23 |
TABLE 5
*M. tuberculosis* Assay
| SAMPLE ID | STRUCTURE | MIC (ug/ml) | SI | ASSAY DATE | EC 90 | EC99 | EC 90: MIC | COMMENT |
|---|---|---|---|---|---|---|---|---|
| 102871 | 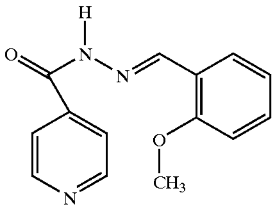 | 0.2 | 500 | 11/12/98 | 0.06 | 0.23 | 0.3 | EC90 RMP = .02; EC99 RMP = .23 |
| 102094 | 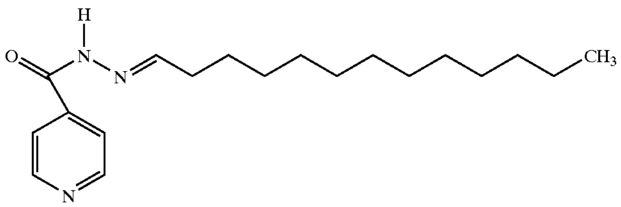 | 0.2 | 374 | 11/12/98 | 0.08 | >3.2 | 0.4 | EC90 RMP = .1; EC99 RMP = .6 |

TABLE 5-continued
| SAMPLE ID | STRUCTURE | MIC (ug/ml) | SI | ASSAY DATE | EC 90 | EC99 | EC 90: MIC | COMMENT |
|---|---|---|---|---|---|---|---|---|
| | M. tuberculosis Assay | | | | | | | |
| 103062 | 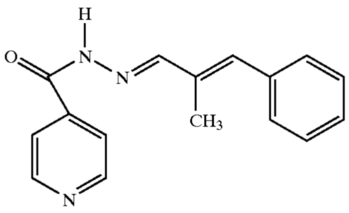 | 0.2 | 250 | 11/12/98 | 0.03 | 0.15 | 0.15 | EC90 RMP = .02; EC99 RMP = .23 |
| 102043 | 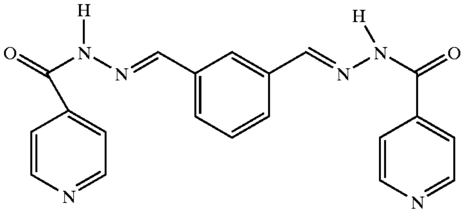 | 0.05 | 126 | 11/12/98 | 0.04 | >0.8 | 0.8 | EC90 RMP = .1; EC99 RMP = .6 |
| 111298 | 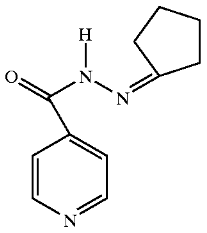 | 0.025 | | 11/17/98 | 0.03 | 0.16 | 1.2 | EC90 RMP = .11; EC99 RMP = .37; EC90 INH = .21; EC99 INH = >.4 |
TABLE 6
| SAMPLE ID | STRUCTURE | ASSAY | MIC (ug/ml) | SI | MIC H37Rv (ug/ml) |
|---|---|---|---|---|---|
| | M. tuberculosis Assay | | | | |
| 102866 | 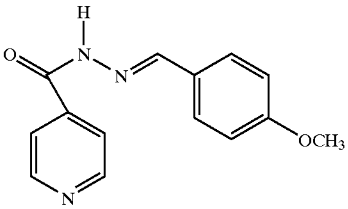 | BACTEC | 0.1 | 1520 | <0.05 |
| 102044 | 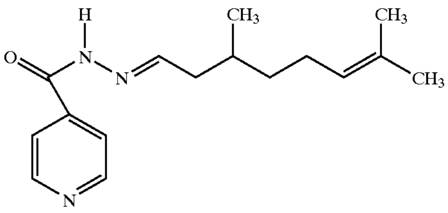 | BACTEC | 0.2 | 1000 | <0.1 |

TABLE 6-continued

*M. tuberculosis* Assay

| | | | | |
|---|---|---|---|---|
| 117150 | 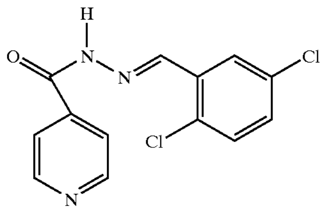 | BACTEC | 0.1 | <0.05 |

| SAMPLE ID | MIC ERDMAN (ug/ml) | MIC INH-R(ug/ml) | INH-R: MIC | MIC RMP-R (ug/ml) | RMP-R MIC | MIC TAC-R (ug/ml) | TAC-R: MIC |
|---|---|---|---|---|---|---|---|
| 102866 | <0.05 | 3.25 | 32.5 | <0.05 | <0.5 | <3.25 | >32.5 |
| 102044 | <0.1 | 3.13 | 15.65 | <0.1 | <0.5 | 3.13 | 15.65 |
| 117150 | <0.05 | >3.25 | >16.25 | <0.05 | <0.25 | >3.25 | >32.05 |

TABLE 7

*M. tuberculosis* Assay

| SAMPLE ID | STRUCTURE | % Inhibition | Test Date | Assay | MIC (ug/ml) | IC50 (ug/ml) | SI | Comment |
|---|---|---|---|---|---|---|---|---|
| 122489 | 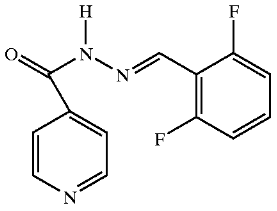 | 99 | 3/2/99 | Alamar | <0.2 | >125 | >625 | MIC of RMP = 0.06 μg/ml. IC50 (INH > 1000; RMP-68; DMSO = 0.0101; DMSO at 1:50 > 1000) |
| 122490 | 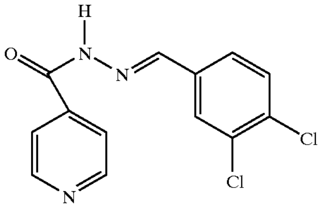 | 99 | 3/2/99 | Alamar | <0.2 | >10 | >50 | MIC of RMP = 0.06 μg/ml IC50 (INH > 1000; RMP = 68; DMSO = 0.0101; DMSO at 1:50 > 1000) |
| 114353 | 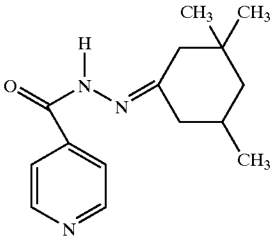 | | | Bactec | >6.25 | | | |

TABLE 8

*M. tuberculosis* Assay

| Sample ID | Structure | MIC (ug/ml) | SI | Assay | MIC H37Rv (ug/ml) | MIC Erdman (ug/ml) |
|---|---|---|---|---|---|---|
| 111992 | 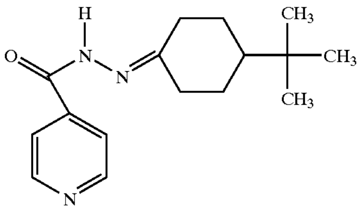 | | >8000 | Bactec | 0.05 | 0.1 |
| 114353 | 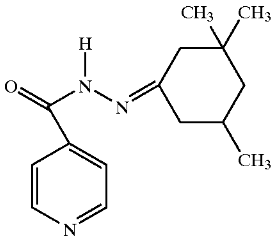 | | >2000 | Bactec | <0.1 | <0.1 |
| 111298 | 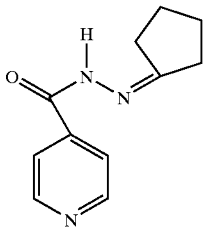 | 0.02 | | Bactec | 0.05 | 0.05 |

| Sample ID | MIC INH-r (ug/ml) | INH-R:MIC | MIC RMP-R (ug/ml) | RMP-R: MIC | MIC EMB-R (ug/ml) | EMB-R: MIC |
|---|---|---|---|---|---|---|
| 111992 | >0.75 | | 0.1 | | 0.1 | |
| 114353 | <6.25 | | <0.1 | | <0.1 | |
| 111298 | >0.75 | >30 | 0.05 | 2 | 0.05 | 2 |

TABLE 9

*M. tuberculosis* Assay

| Sample ID | Structure | MIC (ug/ml) | SI | Assay Date | Assay | MBC vs H37Rv (ug/ml) | MBC vs RMP-R (ug/ml) | MBC vs INH-r (ug/ml) | Comment |
|---|---|---|---|---|---|---|---|---|---|
| 101702 | 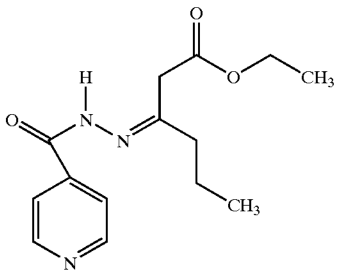 | 0.39 | >2631.6 | 7/15/98 | ALAMAR | >=0.19 | 0.39 | >12.5 | MIC or RMP (ug/ml) vs H37Rv = 0.5; vs RMP-R > 8; vs INH-R = 0.5. |

TABLE 10

| Sample ID | Structure | Test Date | Assay | MIC (ug/ml) | % Inhibition | | Comment |
|---|---|---|---|---|---|---|---|
| | | | | *M. avium* Assay | | | |
| 123668 | 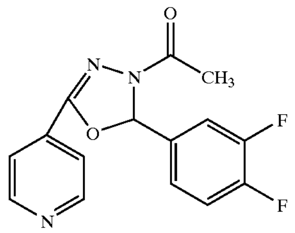 | 12/11/98 | Bactec | <12.5 | 98 | + | MIC Clarithromycin = 2 μg/ml vs. *M. avium.* |
| 123669 | 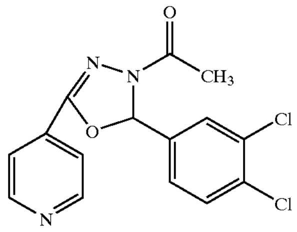 | 12/11/98 | Bactec | >12.5 | 65 | − | MIC Clarithromycin = 2 μg/ml vs. *M. avium.* |
| 122489 | 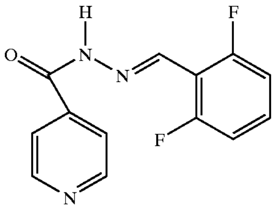 | 12/11/98 | Bactec | >12.5 | 45 | − | MIC Clarithromycin = 2 μg/ml vs. *M. avium.* |
| 122490 | 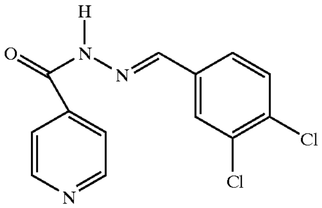 | 12/11/98 | Bactec | >12.5 | 20 | − | MIC Clarithromycin = 2 μg/ml vs. *M. avium.* |

TABLE 11

| Sample ID | Structure | Test Date | Assay | MIC (ug/ml) | % Inhibition | | Comment |
|---|---|---|---|---|---|---|---|
| | | | | *M. avium* Assay | | | |
| 117899 | 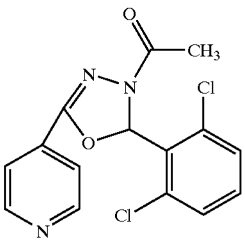 | 9/3/98 | Alamar | >12.5 | 12 | − | MIC Clarithromycin = 2 μg/ml vs. *M. avium.* |

TABLE 11-continued

*M. avium* Assay

| Sample ID | Structure | Test Date | Assay | MIC (ug/ml) | % Inhibition | | Comment |
|---|---|---|---|---|---|---|---|
| 117150 | 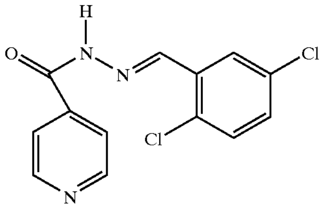 | 9/1/98 | Alamar | >12.5 | 0 | – | MIC Clarithromycin = 4 μg/ml. |
| 126719 | 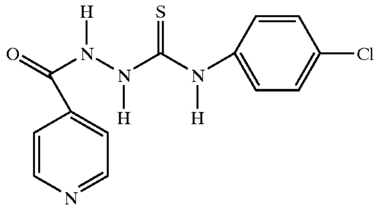 | 9/11/98 | Bactec | >12.5 | 84 | – | MIC RMP = 0.25 μg/ml, 99% inhibition vs. *M. tuberculosis.* |

TABLE 12

*M. avium* Assay

| Sample ID | Structure | Test Date | Assay | MIC (ug/ml) | % Inhibition | | Comment |
|---|---|---|---|---|---|---|---|
| 125304 | 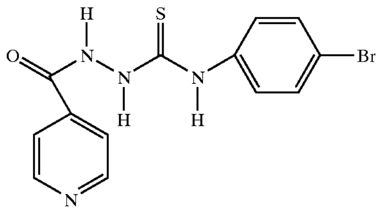 | 7/22/98 | Bactec | >12.5 | 15 | – | MIC RMP = 0.125 ug/ml vs. *M. tuberculosis* |

TABLE 13

*M. tuberculosis* Assay

| Sample ID | Structure | Test Date | MIC (ug/ml) | % Inhibition | Comment |
|---|---|---|---|---|---|
| 122492 | 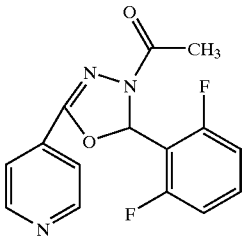 | 5/19/98 | <12.5 | 99 | MIC RMP = 0.25 ug/ml vs. *M. tuberculosis.* |
| 122487 | 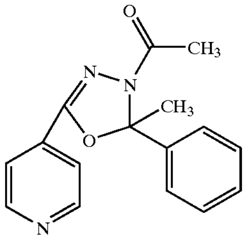 | 5/19/98 | <12.5 | 98 | MIC RMP = 0.25 ug/ml vs. *M. tuberculosis.* |

TABLE 13-continued

M. tuberculosis Assay

| Sample ID | Structure | Test Date | MIC (ug/ml) | % Inhibition | Comment |
|---|---|---|---|---|---|
| 122491 | 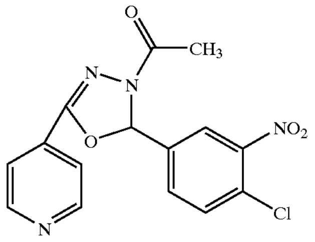 | 5/19/98 | <12.5 | 98 | MIC RMP = 0.25 μg/ml vs. *M. tuberculosis.* |
| 123668 | 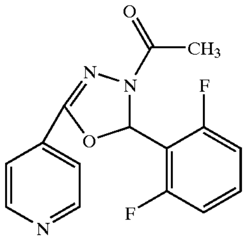 | 5/21/98 | <12.5 | 97 | MIC RMP = 0.25 μg/ml vs. *M. tuberculosis.* |
| 122697 | 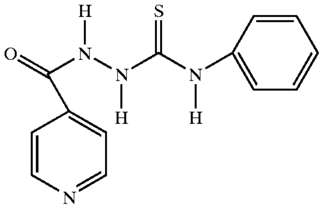 | 5/98/98 | >12.5 | 79 | – MIC RMP = 0.25 μg/ml vs. *M. tuberculosis.* |
| 123667 | 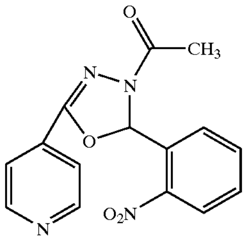 | 5/21/98 | >12.5 | 38 | – MIC RMP = 0.25 μg/ml vs. *M. tuberculosis.* |

In Vitro Testing

Methods for the determination of in vitro activities were used are discussed in detail in the literature. Schoen et al., *Antimicrobial Agents and Chemotherapy,* 42, 3315–3316 (1998). In brief, stock solutions of the drugs were prepared by dissolving them in double-distilled water. Solutions were sterilized by passage through a 0.22-μm-pore-size membrane filter and were diluted 20-fold with modified 7H110 broth, pH 6.6, with 10% oleic acid, albumin, dextrose and catalase (OADC) enrichment and 0.05% Tween 80. Serial twofold dilutions were prepared in modified 7H10 broth, with varying concentrations of drug. Isolates were grown at 37° C. in modified 7H110 broth for 3 to 5 days on a rotary shaker and were then diluted in modified 7H10 broth to yield a final concentration of approximately $2.5 \times 10^4$ CFU/ml. The final volume in each assay tube was 2 ml. The inoculum size was measured by titration and counting from duplicate 7H10 agar plates supplemented with 5% OADC. The isolates maintained an appropriate phenotype on the titer plates. A tube without drug was included as a positive control. Tubes were incubated in ambient air on a rotary shaker (150 rpm) for 5 to 7 days, until good growth was present in the control tube. The MIC was defined as the lowest drug concentration that yielded no turbidity.

| Data | |
|---|---|
| Compound | MIC (*M. avium* 101) |
| MJH-92-I-81 | 1 ug/ml |
| MJH-92-I-87 | 1 |
| MJH-98-I-48c | 4 |
| MJH-98-I-48d | 4 |
| MIC Clarithromycin = 2 ug/ml vs. *M. avium* 101 | |
| Compound | MIC (*M. kansasii swank*) |
| MJH-92-I-81 | 1 ug/ml |
| MJH-92-I-87 | 1 |
| MJH-92-I-48c | 2 |
| MJH-98-I-48d | 1 |
| MIC INH = 1 ug/ml vs. *M. kansasii swank* | |

In vivo Testing against *M. tuberculosis* in a Murine Model

Figure 2:
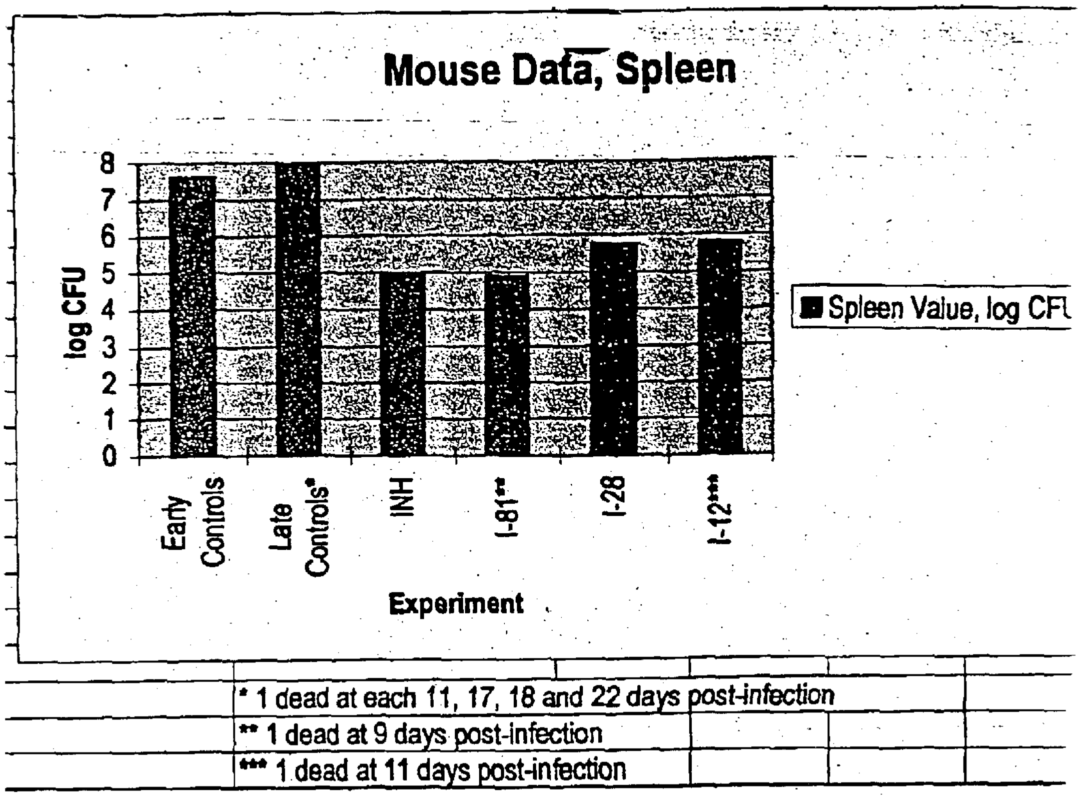
FIG. 2 is a bar graph depicting the in vivo activity of compounds of the invention.

The compounds were evaluated at 25 mg/kg in comparison to INH at a like concentration. Mice were treated 5 days per week by gavage for four weeks. This model, as described in M. H. Cynarnon, Y. Zhang, T. Harpster, S. Cheng and M. DeStefano, *Antimicrobial Agents and Chemotherapy,* 43, 2922–2924 (1999), provides a rigorous test of a compound's antituberculosis activity because of the high inoculum utilized (approximately 10 million viable organisms, Erdman). Referring to FIG. 2, the in vivo activity of one of these compounds was somewhat better than INH against an INH-susceptible organism. In brief, the experiments may be Cn described as follows.

Medium

*Mycobacterium tuberculosis* Erdman (American Type Culture Collection 35801) was obtained from the American Type Culture Collection, Manassas, Va. This strain has been used previously for murine model studies. Klemens et al., *Antimicrobial Agents and Chemotherapy,* 38 1476–1479 (1994); Klemens et al., *Antimicrobial Agents and Chemotherapy,* 40 298–301 (1996). The organisms were grown on modified Middlebrook 7H10 broth, pH 6.6, supplemented with 10% OADC enrichment and 0.05% Tween 80 on a rotary shaker for 5 days at 37° C. The culture suspensions were diluted with modified 7H10 broth to yield 100 Klett units/ml (Klett-Summerson colorimeter; Klett Manufacturing, Brooklyn, N.Y.), that is, approximately $5\times10^7$ CFU/ml. The sizes of the inocula were determined by titration and counting from triplicate 7H 10 agar plates supplemented with 10% OADC enrichment. The plates were incubated at 37° C. in ambient air for 4 weeks prior to counting.

Infection Studies

Six-week-old female CD-1 mice (Charles River, Wilmington, Mass.) were infected intravenously through a caudal vein. Each mouse received approximately $10^7$ viable organisms suspended in 0.2 ml of modified 7H10 broth. There were eight mice per assay group. Treatment was started 1 week after infection. A group of untreated infected mice was sacrificed at the start of treatment (early controls). A second group of untreated mice was sacrificed at the conclusion of the treatment period (late controls). Treatment was given by gavage (0.2 ml) 5 days per week for 4 weeks. Mice were sacrificed by carbon dioxide inhalation at 3 to 5 days after administration of the last dose of drug. Spleens and right lungs were removed aseptically and ground in a tissue homogenizer. The number of viable organisms was determined by serial dilution and titration on 7H10 agar plates. The plates were incubated at 37° C. in ambient air for 4 weeks prior to reading. Viable cell counts were converted to logarithms for comparisons.

All journal articles and reference citations provided above, in parentheses or otherwise, whether previously stated or not, are incorporated herein by reference.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A method for producing an antimycobacterial compound of the formula:

I

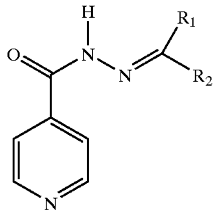

wherein $R_1$ is H; and wherein $R_2$ is phenyl, substituted phenyl, napthyl or substituted napthyl or wherein $R_1$ when taken together with $R_2$ form optionally substituted carbocyclic groups;

which comprises:

refluxing (1)

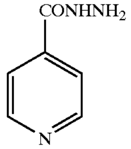

with absolute ethanol to produce a solution;

adding a carbonyl compound comprising the formula of:

$R_3COR_4$ (2)

wherein $R_3$=H; and wherein $R_4$=phenyl, substituted phenyl, napthyl and substituted napthyl; or wherein $R_3$ when taken together with $R_4$ form optionally substituted carbocyclic groups;

to the solution to produce a reaction mixture, the reaction mixture having a mole ratio of carbonyl compound to compound (1) of 1.67 to 1.00;

distilling the reaction mixture;

precipitating a solid from the reaction mixture;

filtering the solid; and drying the solid to obtain I.

2. The method of claim 1 wherein $R_2$ of compound I is phenyl substituted with 1 to 3 substituents selected from the group consisting of a halogen, a hydroxyl, a methoxy, a benzyloxy, a phenoxy, a trifluoromethyl, an isopropyl, and a thiomethyl group.

3. The method of claim 1 wherein $R_2$ of compound I=4-iso-$C_3H_7C_6H_4$, 2,5-di(Cl)$C_6H_3$, 2,3,5-tri(F)$C_6H_2$, 2-F-4-$CF_3C_6H_3$, 3,4,5-tri(F)$C_6H_2$, 2-$Cl_6$-$CH_3O$-iso-$C_9H_4M$, 2-F-3-Cl-6-$CF_3C_6H_2$, 2,4-di($CF_3$)$C_6H_3$, 2,6-di(F)-3-Cl-$C_6H_2$, 2-F-3-Cl-5-$CF_3$-$C_6H_2$, 2-F-5-$C_6H_4$, 2-O—$C_7H_7C_6H_4$, 3-O—$C_7H_7C_6H_4$, 4-O—$C_7H_7C_6H_4$, 2,4,5-tri(F) $C_6H_2$2-F-5-I-$C_6H_3$, 2,3,4-tri(OH)$C_6H_2$, 4-$C_6H_4$—CH═NNHCO-4-$C_5H_4N$, 4-$C_6H_4$-O-$CH_2CH_2CH_2CH_3$, $4\text{-}C_6H_4NO_2$, $2\text{-}C_6H_4OH$, $4\text{-}OH\text{-}3\text{-}OCH_3C_6H_3$, $4\text{-}C_6H_4OCH_3$, $3\text{-}CH_4OCH_3$, $4\text{-}C_6H_4F$, $3,5\text{-di}(CH_3)\text{-}4\text{-}O\text{-}C_7H_7$, $2\text{-}F\text{-}4\text{-}OCH_3C_6H_3$, $2\text{-}ClC_6H_4$, $4\text{-}BrC_6H_4$, $3\text{-}C_6H_4NO_2$, $4\text{-}C_6H_4O(CH_2)_5CH_3$, $2\text{-}Cl\text{-}5\text{-}NO_2C_6H_3$, $4\text{-}Cl\text{-}3\text{-}NO_2C_6H_3$, $2\text{-}C_6H_4NO_2$, $2\text{-}6\text{-di}(Cl)C_6H_3$, $2,3\text{-di}(Cl)C_6H_3$, $3,4\text{-di}(F)C_6H_3$, $2,6\text{-di}(F)C_6H_3$, $3,4\text{-di}(Cl)C_6H_3$ or $4\text{-}C_6H_4Cl$.

4. The method of claim 1 wherein $R_2$ of compound I=

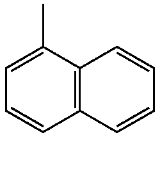
,
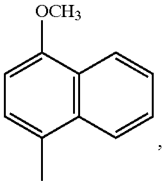
,
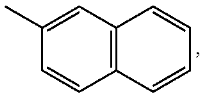
,
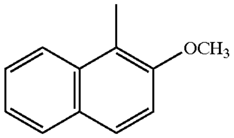
or
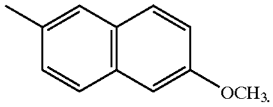

5. The method of claim 1 wherein $R_1$ when taken together with $R_2$ and $R_3$ when taken together with $R_4$ form

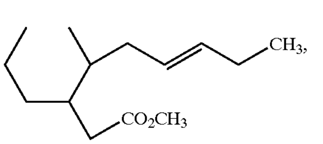
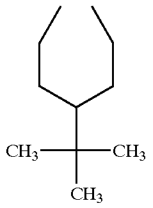
or
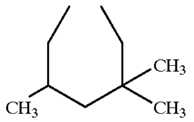

6. The method of claim 1 wherein $R_1$ taken together with $R_2$ and $R_3$ taken together with $R_4$ form $C_4$ to $C_8$ cycloalkyl or $C_4$ to $C_{10}$ substituted cycloalkyl.

7. A method for producing an antimycobacterial compound comprising the formula of:

I

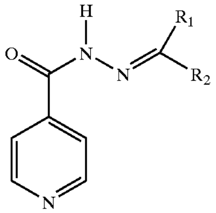

wherein $R_1$ is H or $CH_3$; and wherein $R_2$ is $C_1$ to $C_{14}$ alkyl, $C_2$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, $C_7$ to $C_{16}$ phenylalkyl, $C_7$ to $C_{16}$ substituted phenylalkyl, benzyl, substituted benzyl, heterocycle, substituted heterocycle, halo, hydroxy, amino, or carboxy;

which comprises:

refluxing (1)

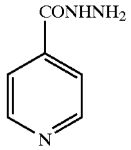

with absolute ethanol to produce a solution;

adding a carbonyl compound comprising the formula of:

$R_3COR_4$ (2)

wherein $R_3$=H or $CH_3$; and wherein $R_{4=C1}$ to $C_{14}$ alkyl, $C_2$ to $C_{10}$ substituted alkyl, $C_2$ to $C_{10}$ alkenyl, $C_2$ to $C_9$ substituted alkenyl, $C_2$ to $C_9$ substituted dialkenyl, $C_3$ to $C_7$ cycloalkyl, $C_3$ to $C_7$ substituted cycloalkyl, $C_7$ to $C_{16}$ phenylalkyl, $C_7$ to $C_{16}$ substituted phenylalkyl, benzyl, substituted benzyl, hererocycle, substituted heterocycle, halo, hydroxy, amino, or carboxy;

to the solution to produce a reaction mixture, the reaction mixture having a mole ratio of carbonyl compound to compound (1) of 1.67 to 1.00;

distilling the reaction mixture;

precipitating a solid from the reaction mixture;

filtering the solid; and drying the solid and obtain I.

* * * * *